United States Patent
Bazaz et al.

(10) Patent No.: US 11,152,114 B2
(45) Date of Patent: *Oct. 19, 2021

(54) PATIENT STATE REPRESENTATION ARCHITECTURES AND USES THEREOF

(71) Applicant: Zyus Life Sciences US Ltd., Saskatchewan (CA)

(72) Inventors: Gaurav Bazaz, Edgewater, NJ (US); Patrick White, Leesburg, VA (US); Cedric Francois, Prospect, KY (US)

(73) Assignee: ZYUS LIFE SCIENCES US LTD., Saskatchewan (CA)

( * ) Notice: Subject to any disclaimer, the term of this patent is extended or adjusted under 35 U.S.C. 154(b) by 1049 days.

This patent is subject to a terminal disclaimer.

(21) Appl. No.: 15/584,249

(22) Filed: May 2, 2017

(65) Prior Publication Data
US 2017/0293700 A1    Oct. 12, 2017

Related U.S. Application Data

(63) Continuation of application No. PCT/US2015/060737, filed on Nov. 13, 2015.
(Continued)

(51) Int. Cl.
*G16H 40/63* (2018.01)
*G06Q 10/00* (2012.01)
(Continued)

(52) U.S. Cl.
CPC ............ *G16H 40/63* (2018.01); *G06F 17/40* (2013.01); *G06Q 10/00* (2013.01); *G06Q 10/103* (2013.01);
(Continued)

(58) Field of Classification Search
CPC ...... G06F 17/40; G06Q 10/00; G06Q 10/103; G06Q 50/24; G06Q 10/063114; G06Q 10/107

See application file for complete search history.

(56) References Cited

U.S. PATENT DOCUMENTS

2005/0144042 A1* 6/2005 Joffe ................. G16H 10/40
705/2
2008/0040151 A1    2/2008 Moore
(Continued)

FOREIGN PATENT DOCUMENTS

WO   WO-2011140095 A1 * 11/2011 ............. G16H 10/60
WO   WO 2014/105752 A1   7/2014

OTHER PUBLICATIONS

Telcare, Inc. and Badgeville Partner to Motivate Patients Living with Diabetes. PRWeb Newswire. Jun. 24, 2013. (Year: 2013).*
(Continued)

*Primary Examiner* — Linh Giang Le
(74) *Attorney, Agent, or Firm* — Frost Brown Todd LLC

(57) ABSTRACT

Using a centralized system, it is possible to allow multiple disparate health care providers to gain a complete view of data regarding a patient's health and health care. Data accessible through such a central system can also be made available for researchers after being de-identified. Data in such a central system can not only include data culled from traditional physical and electronic medical records, but can also include data from distributed diagnostic devices, such as fitness trackers and consumer diagnostic equipment. Such a central system could potentially be accessed through applications made available to patients and health care providers and, in implementations where they are present, such applications could also be used for other purposes, such as performing interactive health evaluations and making recommendations of actions to take to maintain or restore a user's health.

20 Claims, 17 Drawing Sheets

Related U.S. Application Data

(60) Provisional application No. 62/079,372, filed on Nov. 13, 2014.

(51) Int. Cl.
  *G16H 10/20* (2018.01)
  *G06F 17/40* (2006.01)
  *G06Q 10/10* (2012.01)
  *G06Q 10/06* (2012.01)

(52) U.S. Cl.
  CPC ..... *G16H 10/20* (2018.01); *G06Q 10/063114* (2013.01); *G06Q 10/107* (2013.01)

(56) References Cited

U.S. PATENT DOCUMENTS

| | | |
|---|---|---|
| 2011/0246224 A1 | 10/2011 | Green |
| 2012/0253207 A1 | 10/2012 | Sarkar et al. |
| 2014/0006039 A1 | 1/2014 | Khan et al. |
| 2017/0039324 A1 | 2/2017 | Francois |

OTHER PUBLICATIONS

International Search Report and Written Opinion dated Mar. 30, 2016 for Application No. PCT/US2015/060737, 14 pgs.

U.S. Election Restriction dated Aug. 2, 2019, for U.S. Appl. No. 15/202,223, 9 pages.

U.S. Non-Final Office Action dated Apr. 29, 2020, for U.S. Appl. No. 15/202,223, 13 pages.

* cited by examiner

The patient Data Capture Sensor Pool (DCSP) contains all the modules in level 3 of the PIO graph. If a module has multiple parents (such as weight, above), the frequency defined in the PIO is the smallest frequency indicated by all of the parents.

PATIENT STATE REPRESENTATION ARCHITECTURES AND USES THEREOF

CROSS-REFERENCE TO RELATED APPLICATIONS

This application claims priority from, and is a continuation of, international application PCT/US2015/060737, with an international filing date of Nov. 13, 2015, which itself claims priority from U.S. Provisional Patent Application Ser. No. 62/079,372, filed on Nov. 13, 2014. The entire contents of each of these applications are incorporated herein by reference.

FIELD

The disclosed technology can be used for purposes such as facilitating the provision of health care and/or collecting, maintaining and using information about health and health care.

BACKGROUND

Interactions between patients and physicians have traditionally been episodic. Patients typically seek treatment from a physician for newly arising medical conditions and may return to the same physician for follow-up or be referred to a different physician who may then assume responsibility for treating the patient for that condition. Patients may visit more than one physician for the same complaint or consult different specialists for different complaints. Many patients suffer from several chronic diseases, require multiple medications, and are under the care of multiple physicians, who may practice at different health care institutions and may not even be aware that they each care for a particular patient. Additionally, many patients may use health maintenance technology, such as fitness trackers or consumer diagnostic equipment, which could collect data relevant to health care provided by their physicians, but which their physicians may not know exists. As a result of this, health data pertaining to a particular patient or patients is often dispersed among diverse systems, is often organized in diverse manners, may be stored in or reflect information in a variety of different formats, and may not be readily accessible to physicians who are responsible for providing care or to others who could make patients aware of opportunities to improve their health (e.g., people or organizations who could inform a patient that his or her health information indicated that he or she was eligible to participate in a trial of a promising new treatment).

Accordingly, there is a need for technology which can address one or more of the issues associated with the fragmentary and often inaccessible nature of existing health data. Additionally, there is a further need for technology which can assist patients and/or doctors with using information in, and adding information to, medical records for the purpose of improving health care and maintenance. There is a further need for technology which can be used for assembling information in medical records and processing it as appropriate (e.g., de-identifying it) so that it is usable for purposes such as research, as well as for supporting such research and other activities which rely on medical data.

SUMMARY

In some aspects, the disclosed technology can be used to implement systems and methods addressing one or more of the problems or shortcomings associated with existing technology.

In some aspects, a system for analyzing, facilitating access to, and performing actions based on health information is provided. Such a system could comprise a plurality of patient state objects. Each such patient state object could correspond to, and provide a holistic and continuously upgradeable view of, a different patient from a plurality of patients registered with the system. Additionally, each of the patient state objects in such a system could be data structures adapted to store, for the patient to whom it corresponds, data comprising physiological data regarding that patient, behavioral data regarding that patient, and demographic data regarding that patient. Such patient state objects could store all health data used by the system for performing actions for the patients to which they correspond.

In some aspects, each patient state object may be a multidimensional vector accessible using an identifier for the corresponding patient as an argument to a patient state object retrieval function.

In some aspects, in a system which comprises patient state objects storing demographic data for corresponding patients, each the patient state object might store demographic data comprising: age of the corresponding patient; gender of the corresponding patient; income level of the corresponding patient; education level of the corresponding patient; environment of the corresponding patient; and location of the corresponding patient. In some aspects, patient state objects might also store behavioral data for corresponding patients, in which case each patient state object might store the following behavioral data: compliance by the corresponding patient with requests for survey data; compliance by the corresponding patient with using medications as directed; a compliance level score for the corresponding patient; a recent compliance level score for the corresponding patient; a compliance score trend for the corresponding patient; a compliance score volatility for the corresponding patient; and for each of a plurality of body monitors, a compliance score for providing measurements from that body monitor. In some aspects, patient state objects might also store physiological data, in which case each patient state object might store the following physiological data: an overall health score for the corresponding patient; a heath score trend for the corresponding patient; a health score volatility for the corresponding patient; a general hospitalization risk for the corresponding patient; an overall exacerbation risk for the corresponding patient; allergies of the corresponding patient; and medications taken by the corresponding patient. Additionally, in some aspects such physiological data might include, for each of a plurality of conditions, a risk level for the corresponding patient for that condition, and a condition exacerbation risk for the corresponding patient for that condition. Additionally, in some aspects, such physiological data might include, for each of a plurality of body monitors, an urgency score for the corresponding patient for that body monitor, and a risk level for the corresponding patient for that body monitor.

In some aspects, a system comprising a plurality of patient state objects might also comprise a state controller engine ("SCE") having a plurality of rules for updating patient state objects. In some aspects, for each patient state object, such a system may be adapted to cause the SCE to evaluate rules for updating patient state objects based on one or more of: receipt of new data regarding the patient corresponding to that patient state object; and a periodically scheduled trigger for determining updates to that patient state object based on historical data regarding that patient state object. In some aspects, such a system may have only a single SCE, and all updates to all patient state objects may be performed using that SCE. In some aspects, the system may be configured to use the SCE to continuously update the plurality of patient state objects as new data becomes available.

In some aspects, a system comprising a plurality of patient state objects may comprise an action controller engine ("ACE") having a plurality of rules for determining actions to perform based on data from patient state objects. In some aspects, for each patient state object, such a system may be adapted to cause the ACE to evaluate rules for taking action based on data from patient state objects based on one or more of: receipt of a message indicating an update to that patient state object; and a time based trigger for running rules in a batch process. In some aspects, an ACE in such a system may have rules adapted to, based on evaluation of rules with data from a patient state object corresponding to a specific patient, cause the system to perform actions comprising: communicating with the specific patient by sending a message to a computer of the specific patient; communicating with a healthcare provider of the specific patient by sending a message to a computer of the healthcare provider of the specific patient; communicating with a caregiver of the specific patient by sending a message to a computer of the caregiver of the specific patient; requesting health data from the specific patient; requesting an update to a body monitor measurement for the specific patient; recommending that the specific patient take a medication; sending a reminder message to the specific patient; and adjusting a timing or frequency for collecting data from the specific patient. In some aspects, such rules may also comprise rules adapted to cause the system to recommend the specific patient seek medical attention by performing an action selected from a group consisting of calling 911 and calling a physician.

In some aspects, a system comprising an ACE having a plurality of rules may have the plurality of rules organized into a plurality of nodes. In some aspects such a plurality of nodes may comprise a plurality of macro nodes, wherein each macro node is dedicated to a specific rule type and comprises a set of micro nodes. In some aspects, each micro node may comprise one or more rules which, when that micro node is run for a patient, are evaluated with data from the patent state object corresponding to the patient for which that micro node is run; have a single output instruction it could potentially issue upon being run; and have a local priority establishing an order in which it is run in the macro node it is comprised by.

In some aspects, a system comprising an ACE organized into a plurality of macro nodes comprising a plurality of micro nodes may have an ACE configured to perform a smart symptom tracker ("SST") session for a patient by performing a set of acts comprising: running each macro node from the plurality of macro nodes in a predetermined sequence, wherein, for each macro node, running that macro node comprises running the micro nodes comprised by that macro node for the patient for which the SST session is being performed in descending order of the local priorities of those micro nodes; adding all output instructions issued by the micro nodes comprised by the macro nodes while running the macro nodes in the SST session for the patient to a stack; and holding the output instructions issued by the micro nodes comprised by the macro nodes while running the macro nodes in the SST session for the patient in the stack until the SST session for the patient is concluded. Further, in some aspects, such a system may be adapted to after the SST session for the patient is concluded, provide the patient for whom the SST session was performed with information specified by the output instructions added to the stack during the SST session for the patient via an interface on a computing device associated with the patient for whom the SST session was performed.

In some aspects, the SST session may be a virtual SST session. In some aspects, in a system where the SST session is a virtual SST session, the ACE is adapted to evaluate, at initiation of the virtual SST session, a rule for modifying the patient state object corresponding to the patient for whom the virtual SST session is performed to indicate that the virtual SST session is in progress for that patient. Similarly, in some aspects, such a system may be configured to during performance of the virtual SST session for the patient, implement any modifications to the patient state object corresponding to the patient for which the virtual SST sessions is performed triggered by evaluation of rules during the virtual SST session. Also, in some aspects, in such a system the ACE may be adapted to conclude the virtual SST session for the patient by evaluating a rule for modifying the patient state object corresponding to the patient for whom the virtual SST session is performed to indicate that no virtual SST session is in progress for that patient. In some aspects, such a system may comprise an output instructions data structure comprising all output instructions which could potentially be issued by the micro nodes comprised by the macro nodes while running the macro nodes in the SST session for the patient. In some aspects, adding all output instructions issued by the micro nodes comprised by the macro nodes while running the macro nodes in the SST session for the patient to the stack comprises, for each issued output instruction, modifying information in the output instructions data structure for that output instruction to indicate that that instruction should be issued to the patient for whom the virtual SST session is performed. Similarly, in some aspects, providing the patient for whom the virtual SST session was performed with information specified by the output instructions added to the stack during the SST session for the patient may comprise: analyzing the output instructions which information in the output instructions data structure indicates should be issued to the patient for whom the virtual SST session was performed for conflicts; modifying information in the output instructions data structure for any conflicting output instructions to indicate that the conflicting instructions should not be issued to the patient for whom the virtual SST session was performed; and providing the patient for whom the virtual SST session was performed with information specified by the output instructions which information in the output instructions data structure indicates should be issued to the patient for whom the virtual SST session was performed. In some aspects, the output instructions data structure may be an array.

In some aspects, a system comprising an ACE organized into a plurality of macro nodes comprising a plurality of micro nodes may have the plurality of macro nodes comprise a macro node dedicated to triage instruction rules and first in a predetermined sequence. In some aspects, such a macro node may comprise a micro node comprising one or more rules which, when evaluated, could potentially issue an instruction to call 911, wherein the local priority of this micro node is greater than the local priority of all other micro nodes within the macro node dedicated to triage instructions; a micro node comprising one or more rules which, when evaluated, could potentially issue an instruction to call a physician, wherein the local priority of this micro node is greater than the local priority of all other micro nodes within the macro node dedicated to triage instructions, with the exception of the micro node comprising one or more rules which, when evaluated, could potentially issue an instruction to call 911; a micro node comprising one or more rules which, when evaluated, could potentially issue an instruction to take action if there is no improvement after 24 hours, wherein the local priority of this micro node is less than the priority of the micro node comprising one or more rules which, when evaluated, could potentially issue an instruction to call a physician but greater than the local priority of all other micro nodes within the macro node dedicated to triage instructions; and a micro node comprising one or more rules which, when evaluated, could potentially issue an instruction that no triage action should be taken, wherein the local priority of this micro node is less than the priority of all other micro nodes within the macro node dedicated to triage instructions.

Further, in some aspects, in such a system the plurality of macro nodes may further comprise a macro node dedicated to medication instruction rules and be second in the predetermined sequence. In some aspects, such a macro node may comprise: a micro node comprising one or more rules which, when evaluated, could potentially issue an instruction to use a medical device, wherein the local priority of this micro node is greater than the local priority of all other micro nodes within the macro node dedicated to medication instructions; and a micro node comprising one or more rules which, when evaluated, could potentially issue an instruction to take a medication, wherein the local priority of this micro node is greater than the local priority of all other micro nodes within the macro node dedicated to medication instructions, with the exception of the micro node comprising one or more rules which, when evaluated, could potentially issue an instruction to use a medical device. Additionally, in some aspects, the plurality of macro nodes could comprise a macro node dedicated to future instruction rules, wherein at least one micro node comprised by the macro node dedicated to future instruction rules comprises one or more rules which, when evaluated, could potentially trigger a future SST session after conclusion of the SST session being performed for the patient. In some aspects, in such a case the medical device may be a nebulizer, and the medication may be a steroid.

In some aspects, a system comprising an ACE comprising a plurality of rules might organize such a plurality of rules into a plurality of nodes wherein each node in the plurality of nodes: comprises one or more rules; has sequencing data indicating, when data is to be evaluated by rules from multiple nodes, an order of activation for the nodes comprising the rules by which the data is to be evaluated. In some aspects, such a system may be adapted to maintain node type data indicating, for each node from the plurality of nodes, types of data to be evaluated by rules from that node which, in some aspects, might be an index comprised by the ACE. Additionally, when a data item in a patent state object is updated, some systems comprising ACEs with rules organized in this manner may be configured to evaluate that data item with only the nodes indicated by the node type data as comprising rules for evaluating the data type of the data item updated in the patient state object. In some aspects, node type data may indicate a node as comprising rules for evaluating a particular data type by indicating either the node comprises rules which are specific to the particular data type, or the node comprises rules which are general rules applying to multiple data types.

In some aspects, a system comprising an ACE configured to perform an SST session may be adapted to, during the SST session, provide one or more prompts requesting information to the patient for whom the SST session is performed. In some aspects, a system comprising an ACE may be configured to use the ACE to flexibly react to patient data in a real time manner.

In some aspects, the disclosed technology could be used to provide machine comprising: a means for creating, updating and maintaining a patient interface data set, wherein the means for creating, updating, and maintaining a patient interface data set is configured to receive data from a doctor; a means for responding to a patient event, wherein the means for responding to a patient event is configured to receive data from the patient interface data set and communicate with a patient; a means for controlling data, wherein the means for controlling data is configured to receive data from the patient interface data set and write data to a patient data set; a means for maintaining a patient state data set, wherein the means for maintaining a patient state data set is configured to receive data from the patient data set and write data to a patient status data set; a means for consolidating a set of relevant rules, wherein the means for consolidating a set of relevant rules is configured to receive data from the patient status data set and provide data to the means for responding to a patient event; and a means for delivering messages to patients, wherein the means for delivering messages to patients is configured to communicate with the means for responding to a patient event.

BRIEF DESCRIPTION OF THE DRAWINGS

The drawings and detailed description which follow are intended to be illustrative and are not intended to imply limitations on the scope of embodiments or potential implementations of the disclosure set forth herein.

FIG. 14 illustrates global instruction data structures and certain interactions they could be involved in.

DETAILED DESCRIPTION

Figure 1:
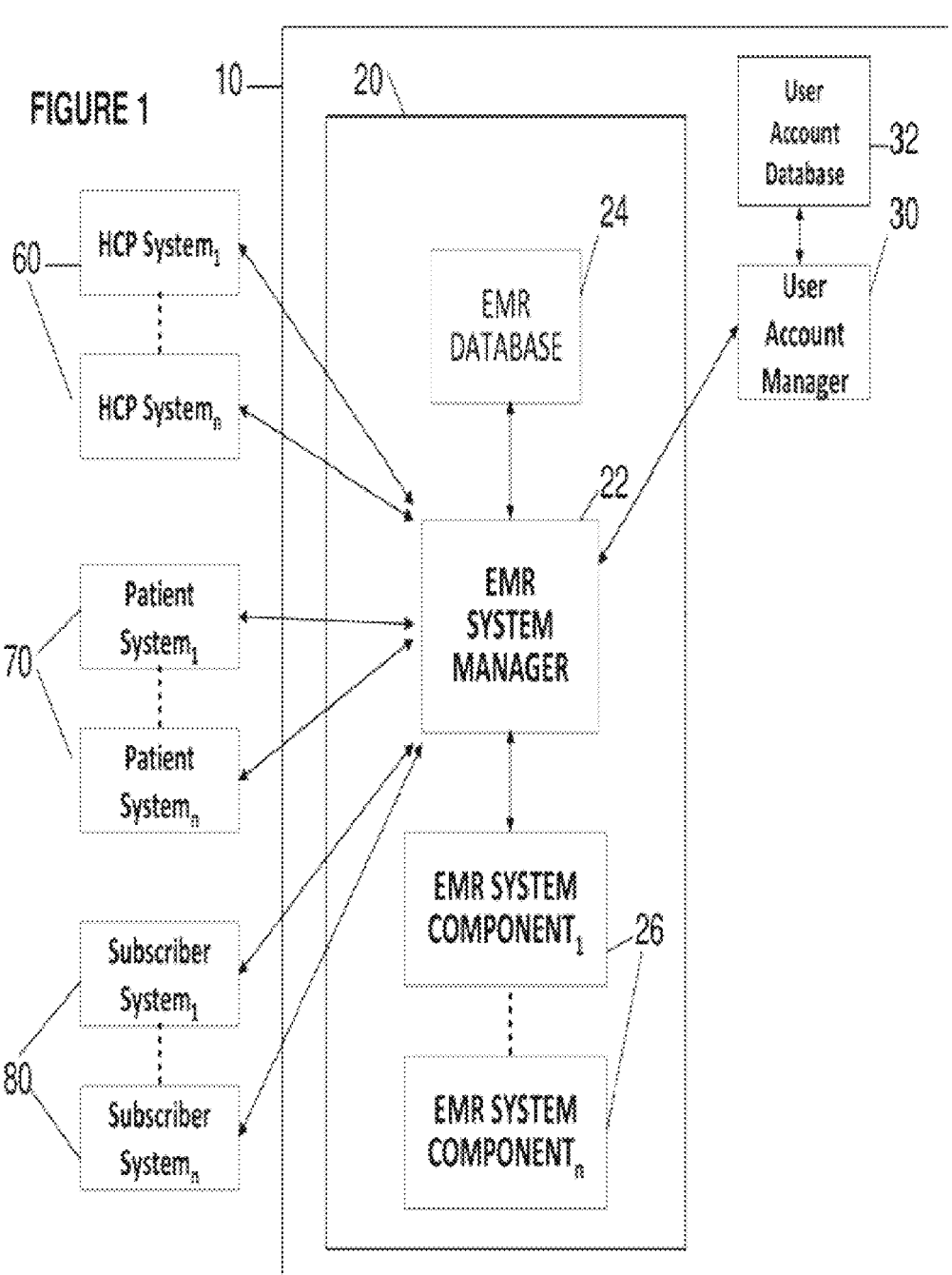
FIG. 1 presents an exemplary high level architecture in which a centralized EMR system serves as a focal point for interactions between a variety of different entities.
Figure 2:
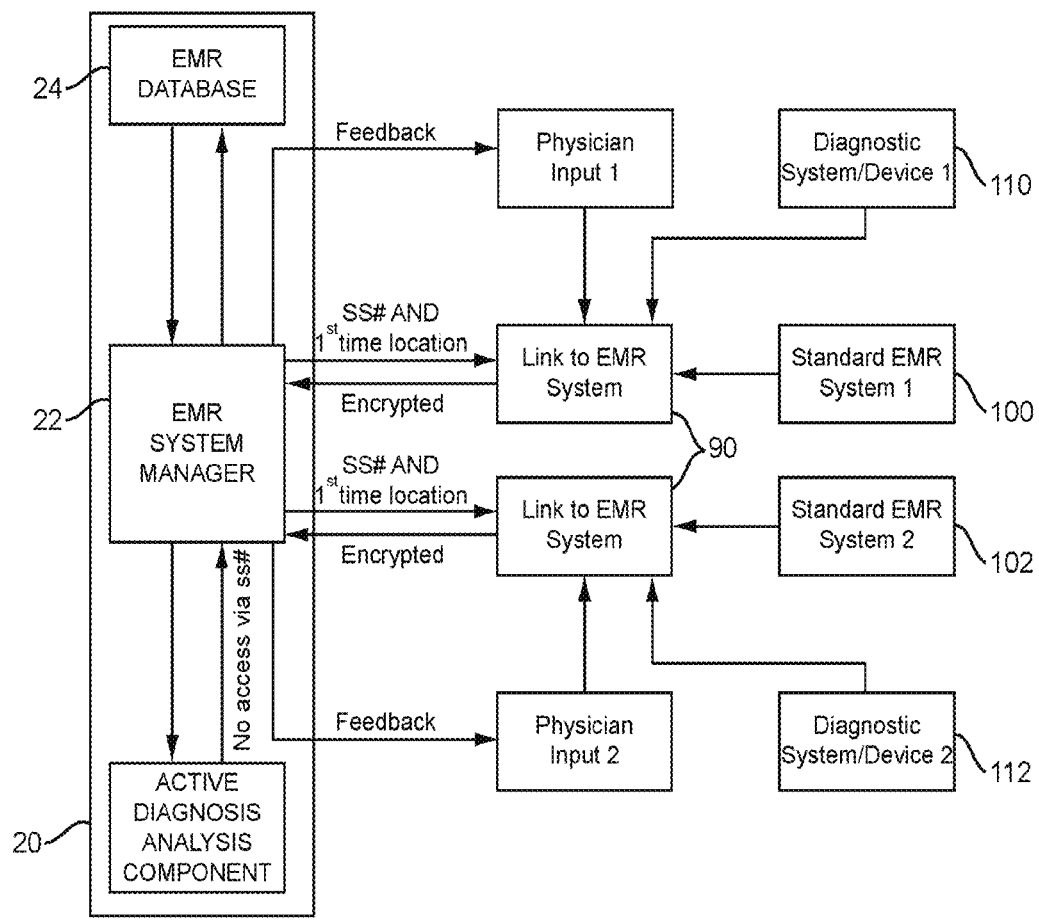
FIG. 2 provides an exemplary high level architecture in which information from external systems such as standard EMR systems can be provided to, and feedback can be received from, a centralized EMR system.
Figure 3:
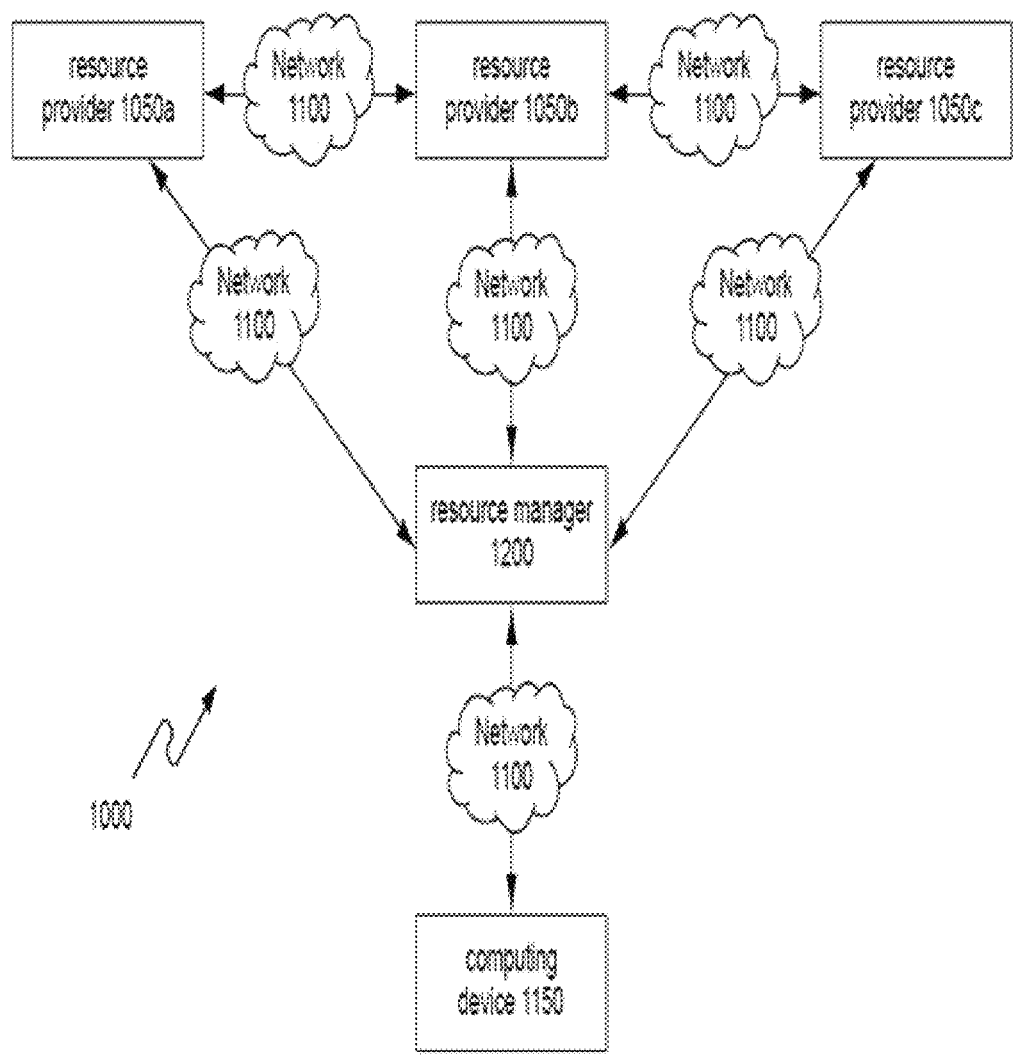
FIG. 3 provides an exemplary high level architecture of a cloud computing environment which could be used in implementing aspects of the disclosed technology.

As will be immediately apparent to those of ordinary skill in the art in light of this disclosure, the technology described in this document can be implemented in a variety of different manners, and using a variety of different architectures. FIGS. 1-3 illustrate architectures which could be used in such implementations. However, it should be understood that other architectures could potentially be used without undue experimentation by those of ordinary skill in the art when implementing aspects of the disclosed technology. Accordingly the architectures of FIGS. 1-3 should be understood as being illustrative only, and should not be treated as implying limitations on the protection accorded by this, or any related, document. It should also be understood that aspects of the disclosed technology may be implemented as an apparatus, machine, computer program product, or combination of any one or more of the foregoing. For example, and without limitation, aspects of the disclosed technology could be implemented at least in part in the form of a computer readable medium having computer-executable instructions stored thereon. It would be understood that a computer readable medium could be non-volatile (retains the stored information even if it is not constantly supplied with electric power) or volatile (requires power to maintain the stored information). Examples of computer readable media that could be used include, but are not limited to, random access memory (e.g., dynamic random access memory, static random access memory), read only memory, non-volatile random access memory, flash memory, hard disk, optical disk, USB flash drive, memory card, and magnetic tape. A computer readable medium could be the main memory of a computer or could be a secondary memory. It would also be understood that health data collected or used by a system implementing the disclosed technology could be stored on a computer readable medium, e.g., in a database.

Turning now to the figures, FIG. 1 presents an exemplary high level architecture in which a centralized electronic medical record ("EMR") system 20, serves as focal point for interactions with a variety of different entities. In an architecture such as shown in FIG. 1, the EMR system 20 can be a system which handles (e.g., receives, analyzes, stores and/or transmits) health information (which term is used interchangeably herein with the term "health data"). The entities (e.g., individuals) which would interact with such a system could include health care providers ("HCPs") and patients and could further include subscribers (e.g., researchers or others who have purchased a subscription to be able to use de-identified health data from the EMR system 20). As shown in FIG. 1, these entities can interact with a centralized EMR system 20 using their own local systems. For example, a physician or other HCP could access the centralized EMR system 20 using a HCP system 60 in the form of a desktop computer which could access a web interface made available via an EMR system manager 22 (discussed infra). Similarly, a patient could access the centralized EMR system 20 via an application on a patient system 70 taking the form of a smartphone, tablet computer or similar device on which the application had been installed. Likewise, a subscriber could access the centralized EMR system 20 through use of a subscriber system 80, which could, for example, be a desktop computer or take the form of a dedicated research terminal. It should be understood that some implementations may not include subscriber systems. While not depicted on FIG. 1, caregivers (who might be family or friends of a patient or might be individuals for whom caregiving is an occupation) could also interact with system 20. Such interaction might be via an application on a patient system a patient system or via an application on a caregiver system, which might take the form of a smartphone, tablet computer or similar device on which the application had been installed.

Implementations of the disclosed technology which follow the architecture of FIG. 1 will often have the capability of supporting an arbitrary (within reason) number of interactions with patients, HCPs, and subscribers. This is shown in FIG. 1 through the use of the subscripts 1-n on the HCP Systems 60, Patient Systems 70, and Subscriber Systems 80. Additionally, the disclosed technology may be implemented in such a manner that the use of specific types of HCP Systems 60, Patient Systems 70 and Subscriber Systems 80 will not be required for interactions with a centralized EMR system 20. For example, while the preceding portion of the disclosure listed particular types of computers (i.e., desktop computers, tablet computers, smartphones, dedicated terminals) for use by different entities in interacting with an EMR system 20, an implementation following FIG. 1 may in some embodiments allow any type of computer to support any type of user interaction (e.g., a patient could interact with the EMR system 20 using a dedicated terminal, a physician could interact with the EMR system 20 using a smartphone to which an appropriate application had been downloaded, etc). Accordingly, the discussion of the various types of entities which could interact with a centralized EMR system 20 in an implementation following the architecture of FIG. 1, as well as the examples of systems which could support those interactions, should be understood as being illustrative only, and should not be treated as limiting. It should also be understood that the principles described herein regarding the various types of entities which could interact with a centralized EMR system 20 also apply in the case of other systems that could be implemented using aspects of the disclosed technology. It should also be understood that a system implementing one or more aspects of the disclosed technology could provide suitable applications and/or user interfaces through which the various users could interact with the system. Different applications and/or user interfaces may be provided that are suitable for use by different types of users (e.g., to support the features and functionality provided to such users). For example, a system could provide an application suitable for use by HCPs (sometimes referred to herein as an "HCP application") and an application suitable for use by patients (sometimes referred to herein as a "patient application"). A system could provide an application suitable for use by other types of users such as caregivers and/or subscribers. Of course it should be understood that an HCP application could in some instances be used by non-HCPs as well as by HCPs. For example, such an application could be used by authorized individuals who work under the direction of an HCP. Likewise, a patient application could in some instances be used by a patient's caregiver or other individual on behalf of the patient. Different applications and/or user interfaces may be provided for different types of computer and/or for computers with different operating systems. It should also be understood that aspects of the disclosed technology could take the form of one or more web applications that could be used on any computer running a compatible browser. The disclosed technology could be used by HCPs of various types, such as physicians, nurse practitioners, physician assistants, nurses, physical therapists, nutritionists, psychologists, and dentists. Where the present disclosure refers to use of the disclosed technology by a physician it should be understood that such description could apply to use of the disclosed technology by HCPs of any type.

As shown in FIG. 1, an EMR system 20 can be made up of multiple components, such as an EMR system manager 22, an EMR database 24, and one or more additional EMR components 26 labeled in FIG. 1 as EMR component$_1$—EMR component$_n$. In an EMR system 20 of the type shown in FIG. 1, the EMR system manager 22 could be used for managing communications and/or interactions. These communications and/or interactions could be either internal to the EMR system 20 (i.e., communications and/or interactions between various components of the EMR system 20 itself), external to the EMR system 20 (i.e., communication and/or interactions between the EMR system 20 and users or external systems), or both. For example, an EMR manager 22 may receive health information from an HCP, transfer the health information to an EMR component 26 for analysis, receive a response from the EMR component 26, and/or transmit the response to a user. An EMR manager 22 might also (or alternatively) include or interface with a database management system ("DBMS") for an EMR database 24. For example, an EMR manager 22 might (via a DMBS) extract information from an EMR database 24 in response to a request from a user, or might add data to the EMR database 24, either in response to a request from a user or in other circumstances (e.g., after the data has been analyzed and approved by a EMR component 26).

Moving on from the discussion of the EMR manager 22, as shown in FIG. 1, an EMR system 20 can also include additional EMR components 26. In some embodiments, these will include an analysis component that analyzes health information received by the EMR system 20. Such analysis may include, for example, determining whether information submitted by an HCP is adequate to meet some predefined set of criteria (e.g., by verifying that a form submitted by an HCP includes all expected information, verifying that a diagnosis submitted by an HCP is accompanied by sufficient diagnostic information for the diagnosis to be reliable, etc). Such an analysis component may provide feedback based on its analysis, which feedback could in turn be transmitted to the user. This feedback could take a variety of forms including, for example, a message to an HCP requesting submission of additional information to validate a diagnosis, or an alert to a patient indicating that information he or she had provided indicates a condition which the patient should take some action to address.

EMR components 26 may also include (either as part of an analysis component or as a separate component) a query component that analyzes and/or processes queries from users (e.g., HCPs, patients, subscribers). For example, such a query component may convert a raw query (e.g., a natural language query) into a format acceptable to a DBMS. EMR components 26 may also (or alternatively) include a clinical decision support system component (CDSS) or an interface thereto, a computerized physician order entry component or an interface thereto, a billing component or an interface thereto, and/or a scheduling component or an interface thereto, etc. EMR components 26 may include one or more components that interface with an application running on a portable electronic device, either directly, or through an EMR manager 22 as described above.

As shown in FIG. 1, an EMR system 20 can be included as part of a larger system 10 which could also include various ancillary components, such as a user account manager 30. A user account manager 30 could also or alternately be an integral component of EMR system 20. In implementations where it is present, such a user account manager 30 may perform any of a variety of functions connected with the administration of user accounts, such as the establishment, maintenance, and/or updating of those accounts. For example, a user account manager 30 may perform functions such as receiving registration information from users, assigning user IDs or passwords, checking login information received from users, etc. User account manager 30 may maintain and/or interface with a user account database 32, which stores user account data. User account manager 30 may be responsible for storing information in, and extracting information from, such a user account database 32, and may also perform similar functions such as analyzing that information or transmitting it to other system components. User account manager 30 may also (or alternatively) have at least partial responsibility for comparing login credentials supplied by users against information stored in user account database 30 and instructing EMR manager 22 to provide, limit, or deny access to the EMR system 20 or portions thereof based at least in part on that comparison. User account manager 30 may also perform other types of tasks related to user accounts or the subscriptions of the associated users (e.g., billing subscribers, transmitting renewal reminders to subscribers, monitoring and controlling use of the EMR system 20 by subscribers, etc.).

Turning now to FIG. 2, that figure provides an exemplary high level architecture in which information from external systems such as standard EMR systems 100 102 can be provided to, and feedback can be received from, a centralized EMR system 20. As shown in FIG. 2, a centralized EMR system 20 may interact with various external systems via links 90 with one or more networks. These external systems may each include one or more computers that may or may not be in communication with one another, though preferably each such system in an implementation following the architecture of FIG. 2 will include at least one device that is capable of communicating with the centralized EMR system 20. Examples of these external systems include (but are not limited to) a computer located in a physician's office (or elsewhere in a health care facility), a computer located in a facility that performs clinical chemistry tests (or any other type of medical tests), a computer that interfaces with or is part of a medical imaging system (or any system used to perform medical tests), a standard EMR system (e.g., a commercially available computer program product for the creation or maintenance of EMRs, such as those listed on the website of the Certification Commission for Health Information Technology or other similar certification body) or a system in which a standard EMR (i.e., an EMR created using a standard EMR system) is stored, a pharmacy system, an electronic prescription system, a practice management system, an appointment scheduling system, a medical billing/claims system (which term refers to a system that performs one or more functions relating to payment for health care (such as generating, submitting, transmitting, processing, or analyzing medical bills or claims for reimbursement for health care services), etc. In some embodiments communication between EMR system 20 and one or more external systems may take place over the Internet.

In an implementation following the architecture of FIG. 1 or FIG. 2, information provided to an EMR system 20 could include a variety of types of information, such as administrative information and health information. For example, in some implementations, in order to establish or access an EMR for a patient, the HCP may be required to enter the patient's social security number ("SS #") (or other identifier), which could then be transmitted to the EMR system 20 in encrypted form. Similarly, an HCP could send various types of health information to the EMR system 20, such as by entering it into the EMR system through a form or similar tool, by having it sent directly from one or more external EMR systems 100 102 via an interface provided by the EMR system 20. In response, the EMR system 20 could provide various types of feedback to the HCP. For example, in response to an HCP providing a SS # (or other information which could identify a particular patient, such as an alternative identifier assigned to the patient for use instead of a SS #) the EMR system 20 could provide feedback in the form of a message indicating whether there was already information for that patient available from or through the EMR system 20. Similarly, in response to an HCP providing information on a recommended treatment for a patient, the EMR system 20 could provide feedback in the form of an alert which could make the HCP aware of a possible interaction between the recommended treatment and a medication which the patient had previously been prescribed. In some embodiments EMR system 20 could additionally or alternately receive information from external systems (e.g., external EMR systems) without requiring action on the part of an HCP. Information entered into an external system may, for example, be automatically transferred to EMR system 20. Such transfer may, for example, occur on a predetermined basis (e.g., daily or weekly) or may be triggered as a consequence of health data being entered into the external system. Additionally or alternatively, EMR system 20 may periodically send requests for updates to external systems.

Thus in many implementations EMR system 20 would not be limited to only receiving data which was entered directly by an HCP or which was already present in some standard EMR system 100 102. For example, as shown in FIG. 2, health information might also be provided to an EMR system 20 by one or more systems or devices (exemplified as diagnostic systems or devices 110 112 in FIG. 2). Such systems or devices could include any of a wide variety of monitoring devices, e.g., personal monitoring devices (e.g., activity tracking devices, diagnostic devices), environmental monitoring devices (e.g., in a patient's indoor environment), etc. For example, software running on a patient mobile device (e.g., a patient's smartphone) could communicate (e.g., via Bluetooth) with a fitness tracker or consumer diagnostic device (e.g., a home glucose monitor) and upload information retrieved from that fitness tracker or consumer diagnostic device to a record for that patient maintained in the EMR database 24 of the EMR system 20. It should be understood that a patient's computer (e.g., smartphone or other portable computing device) or its case may itself serve as a monitoring device. Suitable sensors may be incorporated into the housing of a patient's computer (e.g., smartphone or other portable computing device) or its case. In some embodiments, health information might be uploaded to a server associated with a monitoring device and then provided to an EMR system 20. Various types of health information entry (e.g., via a physical or virtual keyboard, through use of a mouse or other computer pointing device, orally (such as by dictation) through speech recognition software, etc.) could be supported and will be immediately apparent to those of ordinary skill in the art in light of this disclosure. Accordingly, the examples shown in FIG. 2 and provided in the accompanying discussion should be understood as being illustrative only, and should not be treated as limiting. It should also be understood that the examples of external systems and devices shown in FIG. 2 and provided in the accompanying discussion, as well as the types of data that could be obtained from and/or provided to such systems and devices, are illustrative only and should not treated as limiting. Additional or alternative systems, devices, and/or sources of health data could be utilized, and the protection provided by this or any related document should not be limited in this respect. Examples include a practice management system, an appointment scheduling system, a medical billing/claims system (which term refers to a system that performs one or more functions relating to payment for health care (such as generating, submitting, transmitting, processing, or analyzing medical bills or claims for reimbursement for health care services)). In some aspects, the disclosed technology can be used for purposes such as collecting, maintaining and using information relating to payments for health care. For example, bills or claims for reimbursement for health care services could serve as a source of data indicating, for example, that such health services had been provided to a patient. Other sources from which health data may be obtained could include, for example, government or non-government entities that collect environmental data (such as outdoor temperature, levels of pollen or pollutants), population-based data, or epidemiologic data (such as data about the incidence or prevalence of infectious diseases).

Data collected by or provided by a system implementing the disclosed technology could include one or more time stamps. A time stamp could indicate when a particular measurement was made or when a particular input was entered or received.

Turning now to FIG. 3, that figure provides an exemplary high level architecture of a cloud computing environment 1000 which could be used in implementing aspects of the disclosed technology. For example, in an implementation using an architecture such as shown in FIG. 3, an EMR system 20 could be implemented, e.g., in a redundant manner, using various physical components (e.g., databases, servers, etc) managed by one or more resource providers 1050a 1050b 1050c (collectively, 1050). Such resource providers 1050 could provide various hardware and/or software resources used to process data (such hardware and/or software resources being referred to as "computing resources") and could be connected to each other in the cloud computing environment 1000, or could (additionally or alternatively) be connected with one or more computing devices 1150 over a computer network 1100.

To facilitate interaction with the various resource providers, the cloud computing environment of FIG. 3 also includes a resource manager 1200. Such a resource manager 1200 could have a role in the cloud computing environment 1000 similar to that of the EMR manager 22 in the EMR system 20. For example, in operation, a resource manager 1200 might receive a request for a computing resource from a computing device 1150 (e.g., a mobile computing device operated by a patient). It might then respond to this request by identifying one or more resource providers 1050 capable of providing the requested resource (e.g., if the patient requested stored information regarding his or her health, this identification might include determining which resource provider provided storage for health information which could be linked with particular patients) and establishing a connection between one of the capable resource providers 1050 and the computing device 1150 from which the request had been received. In this way, despite the possibility that numerous physical devices might be involved in providing different functionality, the implementation complexity can be hidden from, and therefore be irrelevant to, the various types of end users (e.g., HCPs, patients, etc).

While the discussion of the architectures of FIGS. 1-3 focused on the collection and accessing of health information in the form of EMRs, in some embodiments the disclosed technology could include functionality in addition to (or as an alternative to, as a component of, or independently of) the EMR centralization and retrieval technology which was the focus of the discussion of FIGS. 1-3. As an example of such functionality, consider the possibility of providing condition specific health tracking and management plans. In this document, these plans are referred to variously as T-Plans (treatment plans) or D-plans (data plans), with the terms T-Plan and D-plan being understood as being alternative terms for the same thing. These plans will preferably be assigned by an HCP to a patient and will be stored in a database, e.g., a database similar to that discussed previously with respect to EMRs, thereby providing a convenient way to make it possible for some or all of a patient's HCPs to be able to determine what plans had been assigned to him or her. After being assigned, D-Plans could be used for purposes such as facilitating the collection of data, helping ensure the patient's compliance with a treatment or maintenance program provided by the HCP, and/or facilitating care coordination among multiple HCPs of a patient, to name a few, though, as set forth below, the specific functionality of a D-Plan and the uses to which it could be put will be determined at least in part by the D-Plan's modules, and may vary from case to case.

A system that provides D-Plans, which may be referred to as a "D-Plan system" could have an architecture analogous to the architecture depicted in FIG. 1 wherein a system 20 communicates with multiple HCP systems and multiple patient systems (which could comprise any of the types of computers described above) or an architecture analogous to the architecture depicted in FIG. 2 wherein system 20 also communicates with one or more additional systems that could obtain or store health data of various types or otherwise serve as sources of health data. Such systems or devices could include any of a wide variety of monitoring devices, e.g., personal monitoring devices (e.g., activity tracking devices, consumer diagnostic devices), environmental monitoring devices (e.g., in a patient's indoor environment), etc., as described above in regard to FIGS. 1 and 2. In certain implementations, patients would interact with a D-Plan system using a mobile computing device or desktop computer and HCPs would interact with a D-Plan system using a desktop computer. Alternately or additionally, HCPs may interact with a D-Plan system using a mobile computing device. A D-Plan system could be implemented using a cloud computing environment such as that shown in FIG. 3. A D-Plan system could be implemented independently of an EMR system. In some embodiments such a D-Plan system may communicate with one or more EMR systems, e.g., an EMR system such as EMR system 20. A D-Plan system could obtain data from an EMR system, provide data to an EMR system, or both. A HCP might interact with a D-Plan system using the same computer that he or she uses to interact with an EMR system. Alternatively or additionally, a D-Plan system could be implemented as part of an EMR system, e.g., as part of an EMR system such as EMR system 20.

A D-Plan system could perform any of a wide variety of functions relating to D-Plans. A D-Plan system may, for example, provide functions that permits HCPs to use predetermined templates ("D-Plan templates") to generate D-Plans for patients and to assign such D-Plans to their patients (prescribe D-Plans). For example, a physician who has a patient with a particular condition might assign a D-Plan for that condition to the patient. A D-Plan system may additionally provide other functions such as permitting HCPs to enter data describing patient characteristics (e.g., conditions that the patient has, risk factors for various conditions (such as smoking), etc.), create a patient profile with such characteristics, customize D-Plans for individual patients, create and save new D-Plan templates, etc.

While the disclosed technology will preferably be implemented in a manner which is flexible with respect to the types of modules which would be included in a D-Plan, it is expected that most implementations will have certain types of modules which are present in some (if not all) of their D-Plans. These types of modules can include data collection modules which specify one or more particular type(s) of data to collect (e.g., physiological data such as "weight" or "blood oxygen saturation", health care event data (e.g., data relating to predefined health events, such as results of medical tests) and might also specify a timing (e.g., a frequency) for collecting data of a particular type and modules which provide recommendations (sometimes referred to herein as directions or instructions or advice) to a patient in response to particular health data input by a patient or obtained from monitoring devices. For example, if health data indicate that a clinically significant health change has occurred, the system could recommend to the patient to seek medical attention and/or to take appropriate medication(s). D-Plan modules may further include educational modules which specify educational material to provide to a patient. D-Plan modules may alternatively or additionally include health care event modules which specify particular health care events that have been recommended or prescribed to a patient by a physician. Health care events might include, for example, patient events and/or physician events (as further described below). D-Plan modules might include data collection modules that collect data confirming the occurrence of such health care events and/or collect data arising from such health care events (e.g., results of medical tests). D-Plan modules may also include modules with instructions which could be used in supporting the functions to be provided by those modules for the D-Plan. For example, a data collection module for "blood oxygen saturation" could include data which would cause a computer (e.g., a smartphone running an application which configures it to present questions for a patient) to provide a prompt such as "what is the reading on your pulse oximeter," or to search for and (if found) establish a connection with a patient's pulse oximeter so that the patient's blood oxygen saturation could be obtained directly from that device.

A D-Plan system may configure a D-Plan for a particular condition using a D-Plan template for that condition. Contents of the D-Plan (e.g., the particular modules included in it, particular details of the modules, or both) may be selected based on the condition and, in some embodiments, on patient characteristics. For example, a patient with a particular condition could be assigned a D-Plan for that condition, comprising one or more modules for collection of health data relevant to the condition. A data collection module might, for example, specify collection of physiological data, behavioral data, symptom data, and/or environmental data relevant to the condition. It might specify collection of data elements of a single data element type or multiple different data element types. A D-Plan could also or alternatively include one or more modules for collection of health data, e.g., physiological data, symptom data, behavioral data and/or environmental data pertaining to a patient characteristic relevant to the condition. A D-Plan could also or alternatively include one or more education modules containing educational material relating to the condition or to a patient characteristic that is relevant to the condition. Patient characteristics may be entered by a HCP or otherwise available to the system (e.g., through entry by a patient or from an external system). The D-Plan system may provide a predetermined list of patient characteristics relevant to a particular condition from which a HCP could select those that apply to a particular patient to whom a D-Plan for that condition is assigned. The D-Plan could then be automatically configured to collect health data relating to such characteristics and could take such characteristics into account in the recommendations provided by it.

Data collected according to a D-Plan could be obtained from a patient (or the patient's environment) while the patient is not hospitalized, between the patient's encounters with his or her HCP, and made available to the HCP by the system, thus providing a way for the HCP to gain insight into the patient's health and behavior during the patient's daily life. The system could provide data at least in part in the form of graphics such as plots, charts, etc. Data could also be made available to the patient by the D-Plan system. In some embodiments at least some of the content of a D-Plan assigned to a patient by a patient's HCP, data collected according to a D-Plan, or both, can be viewed by one or more other HCPs who provide care to the patient. For example, the system may provide such HCPs with ability to view a list or description of the D-Plan's modules, data collected by one or more of the D-Plan's data collection modules, or both. Such functionality could be used by HCPs with whom a patient has an existing ongoing relationship, HCPs who may not be familiar with the patient's history (e.g., HCPs who may be seeing the patient for the first time such as HCPs to whom a patient has been newly referred, HCPs in urgent care clinics or emergency rooms, HCPs providing care when a patient's regular HCP is not available, etc.). A D-Plan system might be used by emergency response personnel or other individuals who may need or want to rapidly obtain information regarding the patient's health status or health data.

To illustrate how D-Plans might be assigned and used in patient health care, consider a hypothetical 78 year old patient who has been diagnosed with chronic obstructive pulmonary disease (COPD) and diabetes and who smokes cigarettes. Such a patient could be assigned a D-Plan for COPD by a HCP, perhaps by a specialist in pulmonary medicine. The D-Plan could include one or more modules for collection of health data relevant to COPD, e.g., physiological data such as blood oxygen saturation, behavioral data such as number of cigarettes smoked per day. The D-Plan could also include one or more educational modules containing educational material about COPD. The D-Plan could include an educational module containing educational material relevant to smoking, such as educational material about health risks of smoking or about smoking cessation.

Of course, it should be understood that the separation of D-Plan modules into separate types which perform functions such as collecting data and specifying recommendations to patients in response to health changes is intended to be illustrative only, and that a wide variety of organizations of D-Plan modules is possible. For example, some implementations may include a module (referred to as Smart Symptom Tracker, or "SST"), which could include instructions for collecting data, analyzing that data, and making recommendations or taking actions based on the results of that analysis. In some implementations where they are provided, these SSTs would be condition specific, so that they could easily be added to a D-Plan for a patient based on an HCP's evaluation of the patient's health (e.g., based on a condition that the patient has been diagnosed as having). The data that could be collected by an SST would typically, though not necessarily, include symptom data. Additionally or alternatively, data collected by an SST could comprise other types of health data such as physiological data, behavioral data, environmental data, or other types of data that could be useful in evaluating a patient's health status and determining recommendations. Thus, while the discussion herein of SSTs refers primarily to symptom data, it should be understood that the discussion applies equally to other types of health data. The SST could encode medical knowledge regarding a particular condition, e.g., regarding the significance of particular symptoms, signs, and other types of health data in the context of providing appropriate recommendations to a patient for managing that condition. Such knowledge could be obtained, for example, from health care providers with appropriate training and/or expertise, e.g., HCPs who practice in the specialty that would typically care for patients having the particular condition. In some implementations, recommendations provided by a system could be categorized as "triage" recommendations and "medication" recommendations. A triage recommendation would generally recommend a particular action with regard to seeking medical attention (e.g., seek immediate medical attention, call 911, call your physician, call your physician if your condition does not improve within X hours (for example)). Of course if the system determined that the patient is not in need or potentially in near-term need of medical attention, the system could inform the patient accordingly. A medication recommendation would specify one or more medications that a patient could use (or other patient self-management actions that a patient could take). A patient would typically receive a single triage recommendation at a particular time (though in some instances multiple triage recommendations could be provided if appropriate). A patient could additionally or alternately receive one or more medication recommendations.

To illustrate the role a condition specific SST might have in the management of a patient's health, consider the case of a patient with chronic obstructive pulmonary disease ("COPD"). Such a patient could be assigned a SST designed at least in part to detect a COPD exacerbation, or detect a deterioration that may develop into a COPD exacerbation. This SST (referred to as a "COPD exacerbation SST," though other names could be used as well), could provide instructions which would cause a mobile device used by the patient to perform an interactive health evaluation (e.g., asking questions such as "are you more short of breath than normal", asking the patient to enter physiological data (e.g., measurements of physiological variables) or obtaining such measurements from a personal monitoring device, or both), and then use the results of that evaluation to recommend courses of action to the patient. Such recommendations could include, for example, "I would like you to take one dose of medication X, and call your physician for an appointment" or "you should see a doctor immediately, as the information you have provided may indicate an exacerbation requiring immediate attention." In this way, by assigning a single condition specific SST, an HCP could ensure that the patient's D-Plan included gathering, evaluating and taking actions on, data relevant to the patient's condition. Of course it should be understood that a D-Plan for a particular condition could automatically be configured to include one or more SSTs designed to detect clinically significant health changes relevant to that condition.

Of course, while the above description focused on SSTs which are used (e.g., would be included in D-Plans) for particular conditions, it is possible that some implementations of the disclosed technology could include SSTs which could be used for multiple conditions, or even by multiple health care providers in multiple disciplines. For example, in some implementations, there could be an SST for arrhythmias, which, because arrhythmias are clinically significant for a variety of cardiac disorders, could be included in D-Plans for multiple cardiac conditions. By contrast, a COPD exacerbation SST such as described above would more likely be used in D-Plans for COPD, though their use is not limited to such D-Plans. (For example, a COPD SST might be used in a D-Plan for a different condition, where it might be important to distinguish a COPD exacerbation from an exacerbation of the different condition.) Other relationships, such as where multiple SSTs might be included in a D-Plan for a single condition (e.g., where a particular condition renders a patient prone to multiple distinct types of clinically significant occurrence, in which case a D-Plan for that condition could include a SST for each of those types of occurrence) are also possible and will be immediately apparent to those of ordinary skill in the art. Thus, the discussion above of potential implementations and organizations for SSTs (or other types of modules) within D-Plans should be understood as being illustrative only, and should not be treated as limiting.

It should also be understood that the functions (e.g., collecting data, analyzing that data, and making recommendations or taking actions based on the results of that analysis) of two or more SSTs designed to detect different types of health changes that might occur in patients with a given condition or that might occur in patients with different conditions or in a patient with two or more conditions could be included in a single SST. Such an SST could be designed so as to take into account the potential for overlap between symptoms and signs associated with certain health changes that could occur in the same or different conditions or to distinguish between different health changes that could occur in a single condition. For example, a patient with multiple different conditions could potentially have symptoms that could indicate an exacerbation of either or both of two (or more) conditions. A single SST could be designed to be able to detect an exacerbation of either type.

It should also be understood that in some instances an SST included in a particular D-Plan might analyze and make recommendations based on analysis of data collected by one or more other modules of that D-Plan or data collected by module(s) of one or more other D-Plans assigned to the patient in combination with or instead of data collected by that SST. Such an instance might occur, for example, if other module(s) had already collected some or all of the data required or desirable for the SST to analyze for purposes of making a recommendation (and such data was collected sufficiently recently to remain valid for such purpose). In some instances, execution of an SST might be triggered by the detection of an abnormal value for an element of health data. For example, entry of an abnormally low value for blood oxygen saturation (which could be a sign that a patient is experiencing an exacerbation of a condition that affects breathing such as COPD or asthma) might trigger an SST that collects additional data that could be used to determine whether the patient is having such an exacerbation, analyze the data, and provides a recommendation to the patient based on the analysis. In some instances, a system could provide the patient with the option of executing an SST at any time. A patient might, for example, choose to execute an SST if the patient was concerned about particular symptoms or other health data (e.g., physiological data).

Recommendations to be provided to a patient by a D-Plan system (e.g., by an SST) could have been approved for that patient by the patient's HCP as part of the process of assigning the D-Plan to the patient, which process could include selecting particular medications that the patient would be recommended to use.

As described above, D-Plans can be specialized through the inclusion of appropriate modules for a D-Plan's condition. However, other types of specialization are also possible, and could be supported by a system implemented using the disclosed technology. For example, in some implementations, a base set of D-Plans and/or associated modules might be provided, and HCPs might be given the option of either using the base D-Plans/modules or customizing them for their own use or use by others. These customizations could include adding or removing particular modules or portions thereof, selecting a specific medication from a group of medications, modifications to prompts and/or recommendations which could be provided in performance of a D-Plan (e.g., in execution of an SST) to include the name of the specific patient to whom the D-Plan is assigned, the name of the HCP assigning the D-Plan, or different wording which the HCP believes would be better received or understood by his or her patient population (or any particular patient).

Similarly, in some implementations, the manner for actions to be taken in performing a D-Plan might also be customizable. To illustrate this potential feature, consider the case of an SST which encodes specialized knowledge relevant to a particular condition in the form of weights for symptoms represented by information the SST would collect. In such a case, the SST could use the weights of the symptoms indicated by a patient to determine the urgency of the patient's condition and the recommendations which should be given to him or her (e.g., if the combined weights of the patient's symptoms exceed a threshold for a high priority situation, the patient could be given a message to seek immediate medical attention (e.g., advised to call 911); if the combined weights exceeded a medium priority threshold but did not reach the high priority threshold, the patient could be advised to make an appointment with his or her health care provider, etc.). A doctor might customize the SST by modifying the weight values for particular symptoms, or by changing how those weight values would determine what instructions should be provided (e.g., changing thresholds for determining whether the patient was in a high priority situation). Assigning weights or modifying weights could be performed automatically by the system, e.g., based on physician input. For example, a physician might specify particular health data or combinations thereof that would cause the physician to recommend a particular course of action to a patient. The system might use such input to assign or modify weights. It should be understood that assigning weights to symptoms or other health data and using such weights to determine instructions is but one approach that could be used in implementing an SST.

Of course, other types of customizations are also possible, and could be implemented without undue experimentation by, one of ordinary skill in the art in light of this disclosure.

For example, in a case where an SST reflects specialized knowledge relevant to a condition in the form of a decision tree tying specific statements to particular information a user might provide, customization of the SST could be supported through allowing HCPs to modify the structure of the decision tree or the particular types of information which would cause the SST to traverse its particular branches. Accordingly, the discussion of customization through modification of weights assigned to symptoms or statements which could be provided to a patient should be understood as being illustrative only, and should not be treated as limiting.

While the above discussion of D-Plans focused on how the disclosed technology can provide functionality which would interact directly with a patient to help support his or her health care and/or maintenance, it is possible that the disclosed technology could be used to implement a system which would support similar or additional functionality, which might in some instances be useful for other types of user, as well (or as an alternative to the D-Plans described previously). To illustrate, consider a data structure, referred to as an active diagnosis module ("ADM"), which could be used both to aggregate a patient's health data relevant to a particular condition, and provide one or more schedules comprising condition-relevant events and the times at which such events could take place. Such schedules could include, in addition to, or as alternatives to, actions or behaviors a HCP recommends to a patient as part of patient self-management (referred to herein as "patient events"), actions to be performed by the physician or other HCP or which would otherwise take place in a health care setting (referred to herein as "physician events"). Patient events could include, for example, taking medications, making or attending appointments for follow-up visits with an HCP, making or attending appointments for medical tests such as imaging studies or clinical chemistry tests (e.g., for purposes of monitoring a condition), etc. Physician events could include, for example, follow-up visits, medical tests or other procedures, any other types of health care events that involve interaction with health care In implementations in which they are present, these ADMs and the associated ADM schedules could provide condition-relevant event integration and could function as a centralized store of both health information and treatment plans, while at the same time providing views of relevant events and responsibilities which are customized for particular users and/or user roles. It should be noted that ADMs and/or ADM schedules or one or more features thereof, could be provided as module(s) of a D-Plan.

Figure 4A:
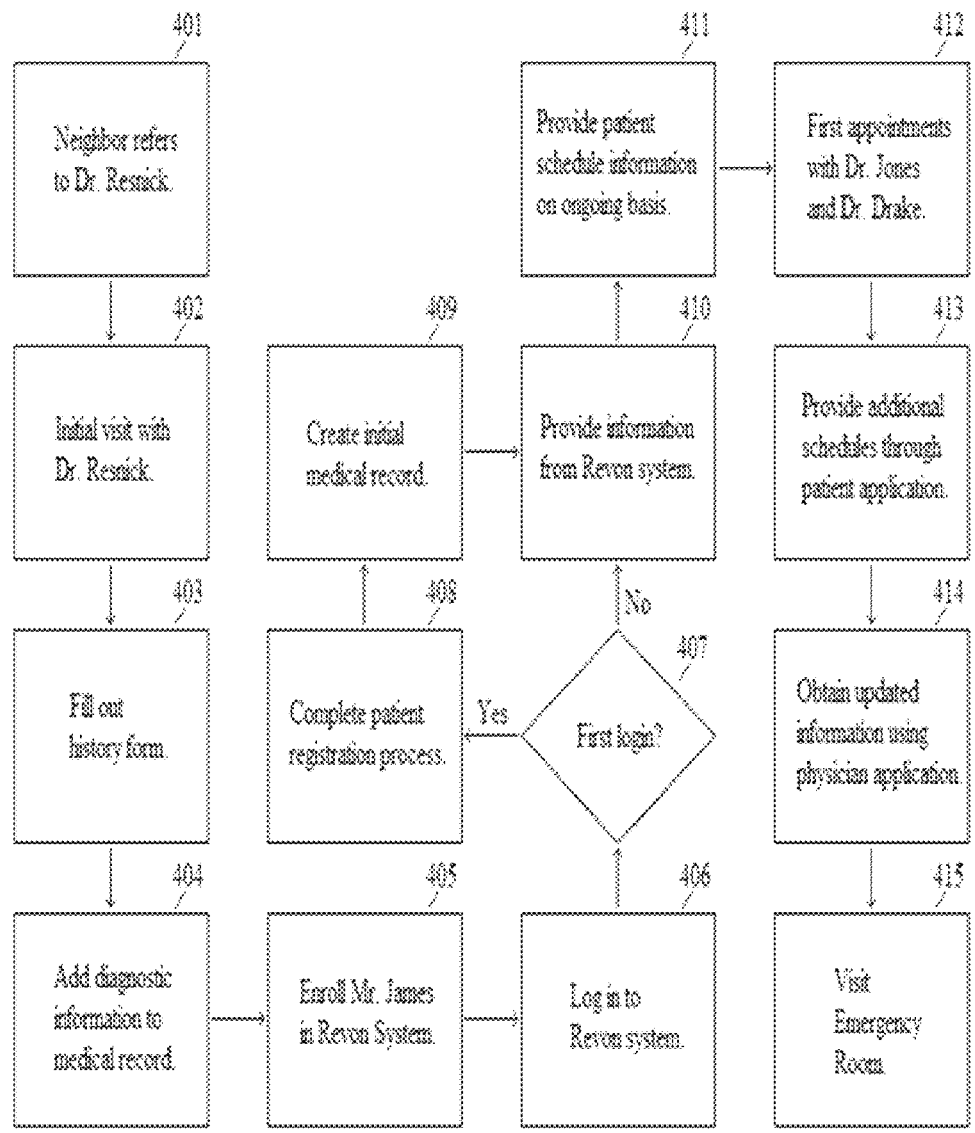
FIGS. 4A-4B provide an exemplary use case in which an implementation of the disclosed technology is used to facilitate health care for a hypothetical 75 year old man with a history of type II diabetes, macular degeneration, and COPD.
Figure 4B:
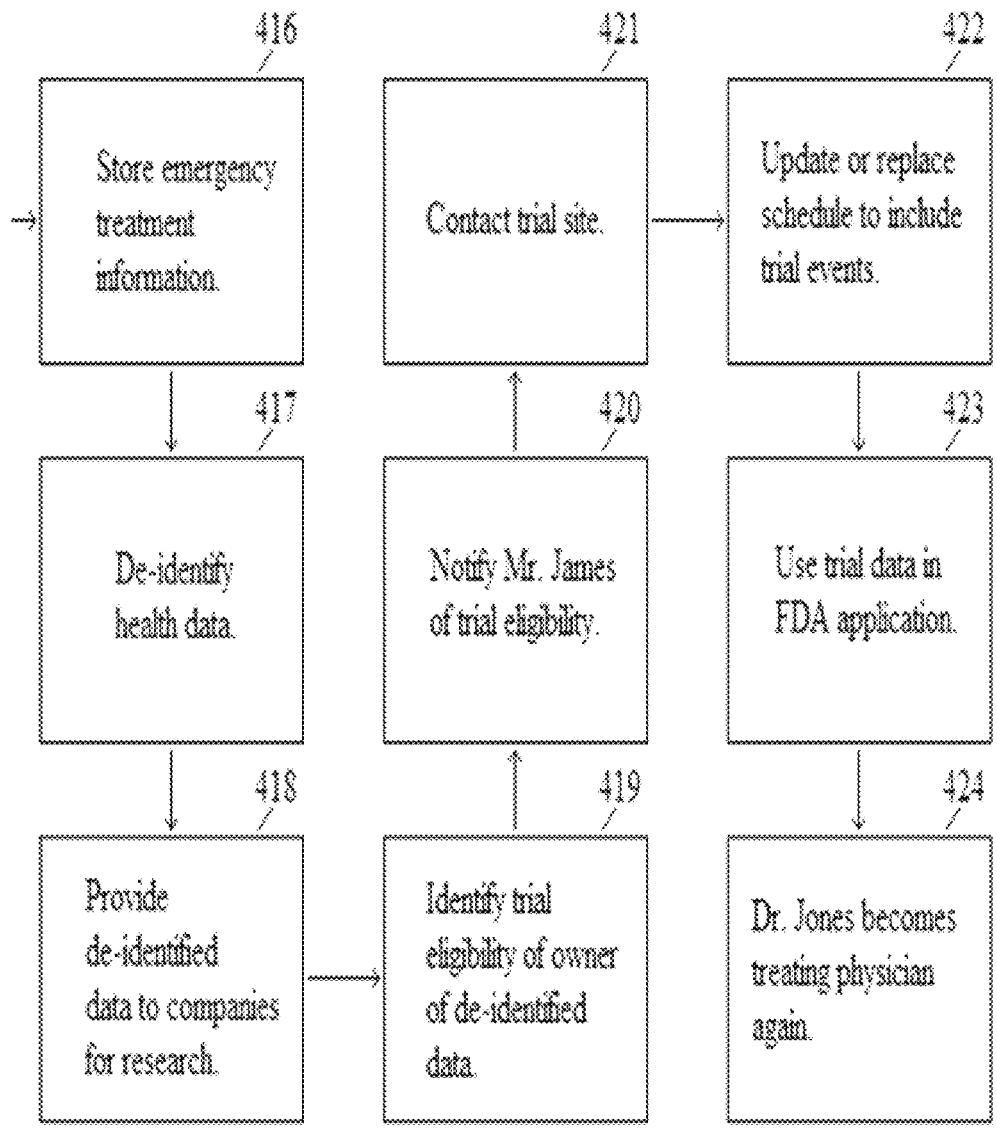

A system implementing or implemented using one or more aspects of the disclosed technology may be referred to as a Revon system (and, correspondingly, the entity maintaining that system may be referred to as "Revon"). A Revon system may, for example, be a D-Plan system, an ADM system, or a D-Plan system that incorporates or makes use of one or more features of an ADM system. To further illustrate how a system implementing one or more aspects of the disclosed technology could be used, consider the following the exemplary use case of FIGS. 4A-4B (which can be combined into a single flow chart by placing FIG. 4B to the right of FIG. 4A), in which an implementation of the disclosed technology is used to facilitate health care for Mr. John James, a hypothetical 75 year old man with a history of type II diabetes, macular degeneration, and COPD. In the use case of FIGS. 4A-4B, Mr. James has recently moved to Louisville, Ky., and needs to find a primary care physician. Therefore, he talks to his neighbor who, in the use case of FIGS. 4A-4B, is already a Revon patient (i.e., a patient who has created or otherwise acquired an account that allows him or her to use a system implemented using the disclosed technology), and his neighbor refers him 401 to Dr. Randall Resnick, a Revon physician (i.e., a physician who has created or otherwise acquired an account that allows him or her to use a system implemented using the disclosed technology). Based on this referral, Mr. James then makes an appointment and visits 402 Dr. Resnick's office for an initial appointment.

While waiting for his appointment with Dr. Resnick, Mr. James fills out 403 a standard medical history form. Dr. Resnick could review the form, and confirm that Mr. James has type II diabetes and convey this diagnosis to an administrator working in his practice who could add the diagnosis, along with information about Mr. James' COPD, to a medical record 404. Dr. Resnick also could also refer Mr. James to a retinal specialist, Dr. Melissa Jones (also a Revon physician), to check for complications of diabetes that can affect the eye and for management of his macular degeneration, and to a pulmonologist, Dr. Frances Drake (also a Revon physician), for management of his COPD. Additionally, in the use case of FIGS. 4A-4B, at the conclusion of the appointment with Dr. Resnick, Mr. James meets with the administrator, who enrolls him in the Revon system 405, and explains features of the Revon patient registration process and the Revon patient application (i.e., an application which Mr. Jones could execute on a mobile device to see his ADM schedule or perform similar activities).

After being enrolled in the Revon system 405, Mr. James could be sent an email with a download for the Revon patient application. Once the application has been downloaded, when Mr. James could use it to log in 406 to the Revon system (e.g., by entering login credentials provided set up by the administrator when enrolling him in the Revon system 405). The application can then check 407 (e.g., by issuing a database call to a central EMR system) if this was the first time Mr. James had logged in. Then, if this was the first time Mr. James had logged in, could perform a patient registration process 408 in which Mr. James would enter information about his medical history, and might also be prompted to provide other information which could be relevant to the care and maintenance of his health (e.g., the names and location of HCPs who had provided care to Mr. James in the past). The Revon system could then use the medical history information provided during performance of the registration process 408, potentially combined with health information obtaining by requesting records from HCPs who had treated Mr. James (e.g., Dr. Resnick) in the past to create 409 an initial medical record for Mr. James.

Once the patient registration process was complete, Mr. James could be provided 410 with information from the Revon system relevant to his health and health care. Such information could include, for example, a type II diabetes ADM Schedule which might have been prescribed by Dr. Resnick during Mr. James' initial visit, and which could include various events that are part of Dr. Resnick's preferred treatment plan for type II diabetes (e.g., medication, monitoring blood glucose level, diet, exercise, and follow-up appointments). In addition to Dr. Resnick's preferred treatment plan, the ADM schedule might also include other customizations, such as if Dr. Resnick had customized his standard type II diabetes ADM schedule for Mr. James's needs by adjusting one or more medication dosages referenced in the schedule. The type II diabetes ADM Schedule could also include other relevant information, such as that Mr. James should return for an initial follow-up appointment with Dr. Resnick in 6 weeks and then every 6 months, and that he should have an annual eye exam.

After Mr. James had been provided 410 with information relevant to his health by the Revon system, the use case of FIGS. 4A-4B continues with the patient application providing 411 Mr. James with patient schedule information on an ongoing basis. This ongoing provision 411 of patient schedule information could take place in a variety of manners. For example, schedule information could be provided using a reactive model, such as if the patient application configured the device used to execute it to allow Mr. James to view his type II diabetes ADM schedule whenever he liked. Alternatively, schedule information could be provided on a proactive basis, such as by providing reminders to Mr. James of events in his schedule (or schedules, such as might be the case if Mr. James had been prescribed a first ADM schedule for type II diabetes, and a second ADM schedule for COPD). Of course combined approaches (e.g., where the patient application could both provide reminders and allow Mr. James to view his schedule) are also possible, and so the description of proactive and reactive models for providing 411 patient schedule information on an ongoing basis should be understood as being illustrative only, and should not be treated as limiting.

Of course, it should be understood that, while FIGS. 4A-4B illustrate the ongoing operation of the patient application in terms of providing patient schedule information, it is also possible that a patient application could be used to provide other kinds of information, or to perform other types of acts, either in addition to, or as alternatives to the ongoing provision 411 of schedule information illustrated in FIGS. 4A-4B. For example, a patient application could be configured to confirm that various acts associated with patient events (e.g., taking medications, monitoring blood glucose level, exercising, and keeping to the diet recommended by Dr. Resnick) had taken place, and could send data indicating that confirmation to the Revon system for storage in a record associated with Mr. James. Similarly, a Revon patient application could also provide Mr. Jones with feedback informing him of his achievements in terms of adhering to Dr. Resnick's treatment program, and might even provide a channel through which Mr. Jones could communicate with other patients who also have type II diabetes. A patient application could also provide certain social functionality, for example, by allowing Mr. James to communicate with networks of people having the conditions (e.g., type II diabetes and/or COPD) he has been diagnosed with. Accordingly, just as the discussion of providing patient schedule information on an ongoing basis should not be treated as implying limitations on providing that information in a reactive or proactive manner, that discussion should also not be treated as implying that ongoing operation of a Revon patient application such as could be used in the use case of FIGS. 4A-4B would be limited to providing information to a patient about his or her schedule(s).

Continuing with the use case of FIGS. 4A-4B, in that use case, a week after the initial visit 402 with Dr. Resnick, Mr. James has his first appointments 412 with Dr. Jones, the retinal specialist, and Dr. Drake, the pulmonologist. Since Dr. Jones and Dr. Drake are Revon physicians, they will have physician applications which can be used to access the Revon system to obtain data about their patients. Accordingly, they will be able to view Mr. James' medical history information, and so Mr. James will not need to complete a paper medical history form for his appointments with either of those doctors and those doctors will already know about Mr. James' existing conditions and treatments (e.g., that he has type II diabetes and has been prescribed Dr. Resnick's type II diabetes ADM schedule). They will also be able to customize and prescribe additional ADM schedules for Mr. James as they see appropriate. For example, Dr. Jones could prescribe an ADM schedule which includes events that are part of her treatment plan for macular degeneration, and Dr. Drake could prescribe an ADM schedule which includes events which are part of his treatment plan for COPD. These schedules could then automatically be provided 413 by the Revon system to Mr. James through his patient application which, from that point on, could display the condition-specific schedules so that Mr. James can see the events for each condition and an integrated schedule that displays events for the three conditions in a consolidated manner.

Just as a Revon physician application could be used by Drs. Jones and Drake to obtain information in preparation for their initial appointments with Mr. James, that application could also be used by Dr. Resnick to obtain 414 updated information on Mr. James' health and health care for use during Mr. James' follow up visits. Thus, in the use case of FIGS. 4A-4B, on the day of Mr. James's next appointment, Dr. Resnick can use the Revon physician application to review Mr. James's self-reported adherence to his recommendations pertaining to medications, monitoring blood glucose level, diet, and exercise. During the appointment, Dr. Resnick can use this information as the basis of a discussion with Mr. James regarding how he could improve his self-management of his condition. The Revon physician application could also inform Dr. Resnick of events which took place during the appointments with Drs. Drake and Jones (e.g., confirming that an eye exam scheduled as a physician event by Dr. Resnick had taken place during Mr. James' appointment with Dr. Jones), and that Mr. Jones now has a macular degeneration ADM Schedule and a COPD ADM Schedule. In this way, the disclosed technology can be used to assure an enrolled HCP that a patient is receiving treatment for his or her diagnosed conditions, and that the various events needed to address those conditions have taken place.

Subsequently (e.g., later that year), the use case of FIGS. 4A-4B continues with Mr. James, while visiting his son in Denver, Colo., suddenly starting to feel short of breath and visiting 415 an emergency room. In this case, the emergency room physician is a Revon physician and is able to access Mr. James's Patient Medical History in the Revon system, thereby learning immediately that Mr. James has a history of COPD and which medications he is taking. In the emergency room, a chest X-ray is taken and Mr. James is given oxygen, and each of these emergency room treatment events could be stored 416 by the Revon system in its records for Mr. James. Then, during Mr. James' next appointment with Dr. Drake, Dr. Drake could see that Mr. James visited the emergency room and that a chest X-ray was taken, and could ask Mr. James about the event in order to determine whether he has had further episodes that may require adjustment of the treatment plan.

Meanwhile, in addition to being used as described, in the use case of FIGS. 4A-4B, the data from Mr. James' three ADM schedules (as well as other data from the Revon system) is de-identified 417 and provided 418 to subscribing pharmaceutical companies for use in developing new medications. The use case continues with one of these companies which is looking for subjects for a clinical trial of an experimental therapy for macular degeneration, identifying 419 Mr. James's de-identified ADM as an ADM of an individual who is eligible for the trial. The system could then notify 420 Mr. James (e.g., with an alert which could be provided to Mr. James next time he opens the patient application) of his eligibility. This notification could not only inform Mr. James of his eligibility, but could also provide him with certain additional information, such as the therapy which is the subject of the trial, the dates on which the trial takes place, and the contact information for the site where the trial will be conducted.

After this notification, the use case of FIGS. 4A-4B continues with Mr. James contacting 421 the site and making an appointment to be screened. Mr. James then enrolls in the trial and the ADM schedule for macular degeneration is updated or replaced 422 by one that includes the various events required by the clinical trial protocol. Additionally, the records for Mr. James maintained by the Revon system can be updated to indicate that, during the trial, the principal investigator on the trial is the treating physician for the macular degeneration ADM, and the ADM schedule containing the clinical trial events could be used instead of the macular degeneration ADM schedule from Dr. Jones. Such a clinical trial ADM schedule could, among other things, remind Mr. James of the medical appointments related to his participation in the clinical trial. It could also be used to collect patient-reported outcomes of treatment. Finally, once the trial is complete, the pharmaceutical company that sponsored the clinical trial would use 423 the data in its application to the Food and Drug Administration for approval of the new therapy, and Mr. James could return to being treated by Dr. Jones, who would become 424 the treating physician for his macular degeneration ADM once again.

Of course, it should be understood that, while the above discussion of the use case of FIGS. 4A and 4B was intended to illustrate how data structures such as ADMs and ADM schedules could be integrated into a system implementing the disclosed technology, variations on the approaches described in that discussion are possible, and so that discussion should not be treated as limiting on the scope of protection provided by this or any related document. For example, while the discussion of FIGS. 4A and 4B included separate steps for a patient to be enrolled 405 by an administrator and to register 408 when he or she first logs into the patient application, the disclosed technology could be implemented in such a manner as to make such separate enrollment 405 and registration 408 unnecessary (e.g., the creation 409 of the initial medical record for the patient could happen during enrollment 405 rather than the initial medical record only being created later at registration 408). Similarly, while the discussion of FIGS. 4A and 4B focused on implementations of the disclosed technology which used ADMs and ADM schedules, similar processes could take place in implementations where those particular data structures were absent (e.g., the functionality described for the patient application in the context of ADMs, such as providing reminders of upcoming events, could alternatively be provided by other types of data structures, such as SSTs).

Variations are also possible in terms of how various components such as described in the context of FIGS. 1-3 could operate to provide functionality such as described in the context of FIGS. 4A-4B. For example, consider the execution of instructions for making recommendations or taking actions based on the analysis of health data which was discussed in the context of SSTs. In some implementations, these instructions would be executed on a mobile device running a patient application which had been suitably configured using an SST, ADM, or other similar data structure. However it is also possible that the disclosed technology could be implemented to execute those instructions on a central system which a user would interact with using a browser or some other type of general purpose interface application. Accordingly, it should be understood that particular approaches described for distributing processing and other responsibilities among devices used to implement the disclosed technology are intended to be illustrative only, and should not be treated as limiting.

A number of variations and modifications might be adopted by those of ordinary skill in the art when implementing one or more aspects of the disclosed technology. For example, aspects of the disclosed technology could be implemented in a patient centric manner. An illustration of this is provided in FIG. 5, which depicts a high level architecture which could be used to manage data and trigger actions on a virtual representation of a patient, illustrated in FIG. 5 as a "Patient State Object" (PSO) 501. As described in more detail below, an architecture such as illustrated in FIG. 5 can be implemented to use a virtual representation of a patient as a centralized location for patient information, with components such as a state controller engine 502 (which could use a first set of rules to determine how to update a patient's virtual representation upon receipt of new data) being used to make sure a patient's virtual representation is up to date, and an action controller engine 503 (which could use a second set of rules to determine what actions should be taken after being triggered by an update in the patient's virtual representation) to determine what types of actions the system should take.

Figure 5:
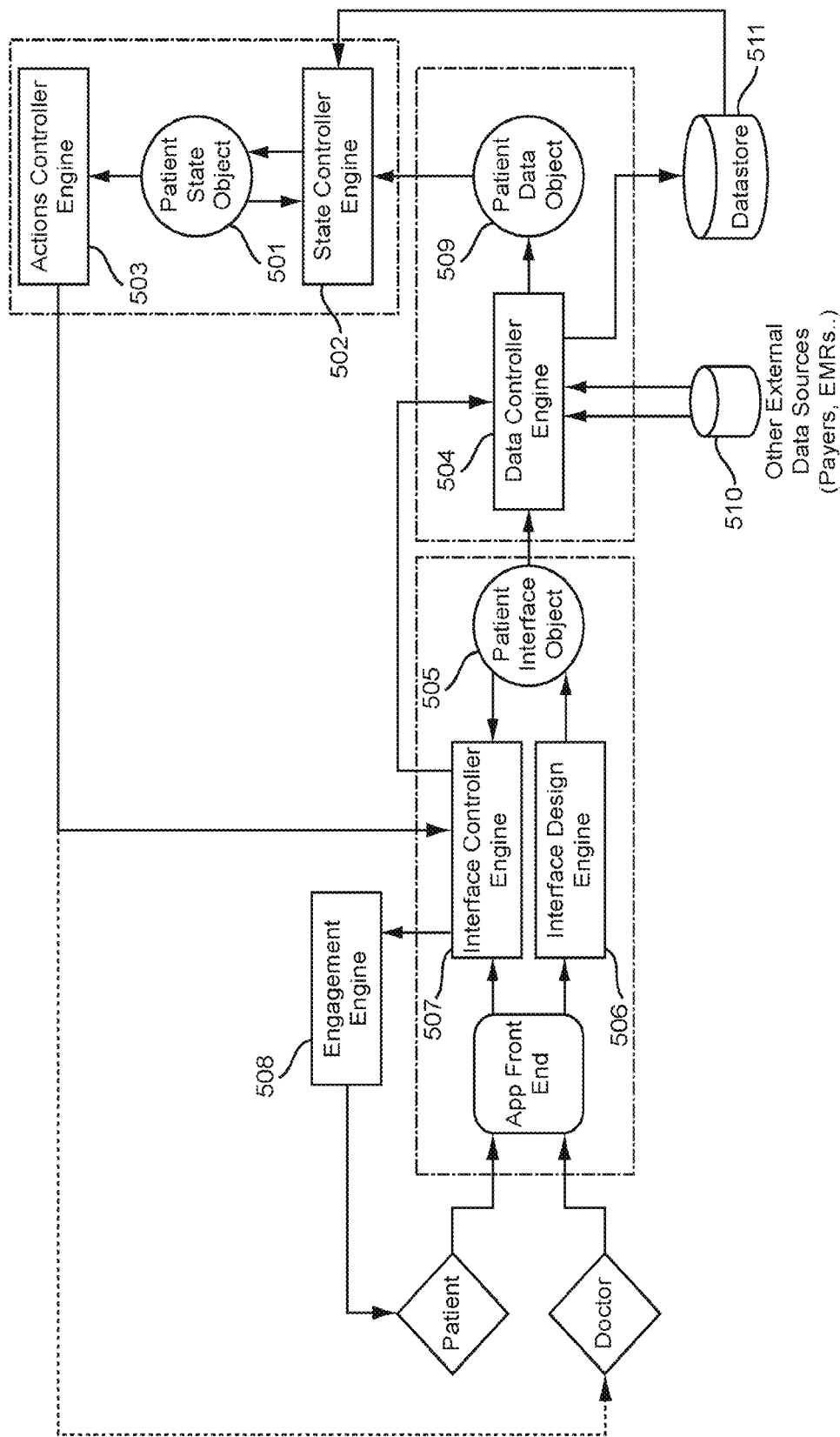
FIG. 5 depicts a high level architecture which could be used to manage data and trigger actions on a virtual representation of a patient.

Turning now to a more detailed discussion of the individual items illustrated in FIG. 5, a patient state object 501 might include any of a wide variety of types of information that are relevant or related in some way to the patient's health. Such information could comprise individual data elements such as recently gathered physiological data, behavioral data, environmental data, and the like, e.g., data element types that could indicate that a particular action should be triggered. Information in a PSO 501 would often include demographic information (e.g., age, gender, income level, education level, and the like). At least some implementations of a PSO 501 could include one or more risk levels. Such risk levels might be derived based on, e.g., a patient's: medical history (e.g., past health care events such as past hospitalizations), past and/or current conditions (e.g., their identity, severity, etc.), family history, genotype, environment, compliance (e.g. with requests from the system for entry of data, with using medications as directed, or the performance of any other health-related actions that could be tracked by the system (e.g., through a mobile device)), demographic factors, social factors, volatility in health data measurements. A PSO 501 could include general risk levels that are not specific to a particular condition (e.g., they are relevant to the patient's overall health or to at least a substantial proportion of the conditions that the patient has), condition-specific risk levels, or both. Condition-specific risk levels could be a function of severity of the condition, relevant comorbidities, medical history with respect to that condition, among others. Elements in a patient state representation might be derived from multiple different data elements or data element types. For example a risk level could be derived from multiple data elements for that patient.

To store this information, a patient state object 501 could be implemented as a multi-dimensional vector reflecting the current understanding of the patient's health state. An example of a multidimensional vector patient state object 501 is provided below in table 1.

TABLE 1

Exemplary vector representation of a patient state object

```
PSO(patient_k) = {
    [overall_health_score,      health_trend,      health_score_volatility,
    gen_hospitalization_risk, ..],
    [compliance_level,      recent_compliance_level,      compliance_trend,
    compliance_volatility, BM1_compliance,
    BM2_compliance..],
    [disease_x_risk_level, disease_y_risk_level, comorb_x_risk_level, ..],
    [BM_overall_risk_level, BM_1_risk_level, BM_2_risk_level,..],
    [BM_1_urgency, BM_2_urgency, ..]
    [overall_exacerbation_risk,                disease_x_exacerbation_risk,
    disease_y_exacerbation_risk, ...]
}
```

Such a vector could be seen as a multi-dimensional health score for a patient, and, as will be apparent in light of this disclosure, could reflect all relevant aspects of patient health.

The following description of an exemplary indicative operation of a patient state object 501 and related items further illustrates the role that a patient state object 501 could play in a system following the architecture of FIG. 5. Initially, when a patient creates an account with the entity operating the system (or when such an account is created for a patient by some other person or entity, such as would be the case in embodiments where a patient account could be completed at least in part by HCP personnel, Revon personnel, or automatically from existing EMR data), the patient will provide basic information about himself or herself (e.g., name, social security number, phone number, email address, and mailing address) and a patient state object 501 will be created for that patient and will be initiated in a default state (e.g., a null state). As the patient completes a profile, his or her patient state object 501 will be updated based on the profile data the patient provides. This could comprise:

Updates based on medical data (allergies, medications (e.g., type, dosage, frequency, generic or brand, etc), any medical history they provide)

Updates based on demographic data—age and/or date of birth, location/neighborhood, income level, education level etc.

Further updates, reflecting disease and comorbidities, can take place once the patient gets his or her first D-plan. Subsequently, updates can take place based on BM data, edu interactions, SST interactions. Such updates may comprise:

Using raw measurement data (BP, pulse, SpO2, weight) as it comes in from BMs to update the PSO 501

Using interaction data, as it comes in, to update the PSO 501 (% requests completed, time to respond, etc.)

When SST runs: data gathered by an SST, will feed back into patient state, and update it in near real time Actions to be executed based on the available data about the patient may be executed by the Actions Controller Engine 503 (discussed in more detail infra). This module may run when the PSO 501 is updated and may have a set of rules for determining if any action should to be taken based on current patient state. In some embodiments, an ACE 503 may be configured to look across lot of parameters very easily to make decisions. For example, in some embodiments, to trigger an SST it can look at certain BM values, recent patient compliance level, exacerbation risk for related disease, and then decide. Actions may include one or more of:

Request another BM or update to a BM

Request an SST to be run

Issue instruction to patient (call doctor's office, call 911 . . . )

Send reminder to patient

Send edu material to patient

Send notification to physician

Send notification to caregiver (relative, friend) . . .

There may be one or more sets of rules, which may be same as rules for SSTs and BMs for triggering instructions and actions. These sets of rules may include rules for the SCE 502 (discussed in more detail infra), which determines how the PSO 501 is updated based on the incoming raw data about the patient. They may also include rules for the ACE 503, which could control what actions are triggered by the ACE 503 based on the PSO 501. Embodiments using the architecture described herein may allow ACE 503 rules to leverage all the data about a patient, rather than being limited to one measurement or SST (which might be the case for some other embodiments), creating a split between the interpretation of the raw data from the actions executed based on the data. Additionally, in some embodiments, SSTs may ask questions and gather data, but will not issue instructions themselves. Their data will update the PSO 501, and the ACE 503 will issue instructions based on the updates to the PSO 501. In such embodiments, the actions will preferably reflect the available data about the patient (captured in PSO 501) and not just what this SST run captured.

The patient state representation (e.g., a PSO 501) could be designed to closely reflect the actual state of the patient's health, such that, for example, when the patient state representation of a particular patient shows a certain risk of hospitalization in percentage form, approximately that percentage of patients (e.g., ±5%), with the profile of the particular patient, would in fact be admitted to the hospital over a period of time. In some aspects, an implementation that utilizes a patient state representation could provide flexibility and enhanced functionality in any of a variety of ways. For example, it could allow a system to incorporate a wide variety of relevant information in determining recommendations (which information could include both individual data elements as well as longer term metrics such as trends, risk levels), allow for flexibility in the system's behavior (e.g., providing for follow-up in instances in which the system has recommended that the patient take particular actions or in which the system has detected a concerning trend in the patient's health status), etc. Of course these are but a few examples illustrative of capabilities that a system implementing a patient state representation could have. It should also be understood that an implementation of a patient state representation could be used for a variety of other purposes in addition to, as part of, or instead of in providing or facilitating provision of health care to a patient or implementing a patient health tracking and management system. For example, a system implementing a PSO 501 could be used to predict the future health or health care utilization of a patient or population of patients, simulate the effect of particular health care interventions on a particular patient or population of patients, identify patients who would benefit from particular health interventions, etc. Such uses could be implemented as part of a system that provides or facilitates provision of health care to a patient (such as a patient health tracking and management system) or could be implemented as an independent system.

Figure 6A:
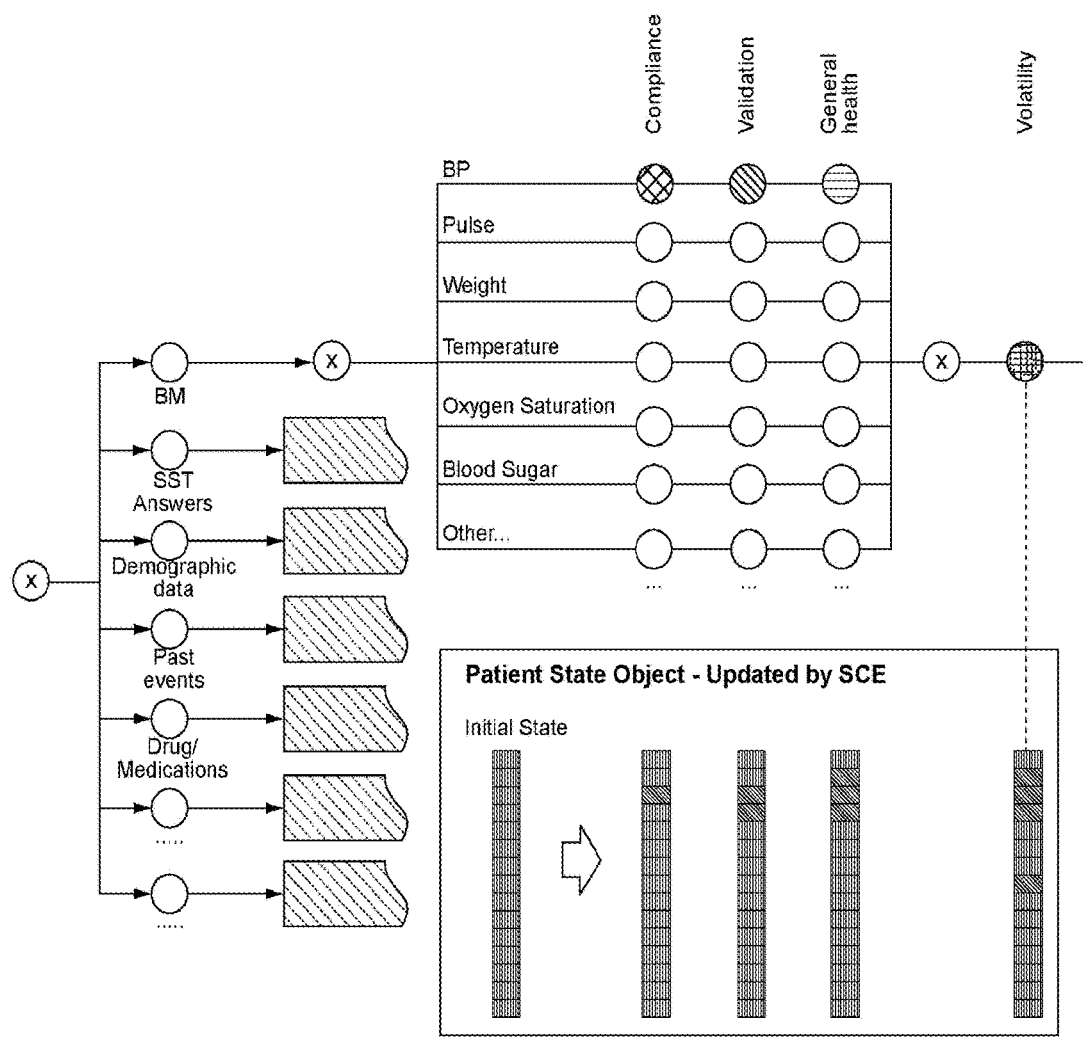
FIGS. 6A-6B illustrate how a state controller engine could update a patient state object.
Figure 6B:
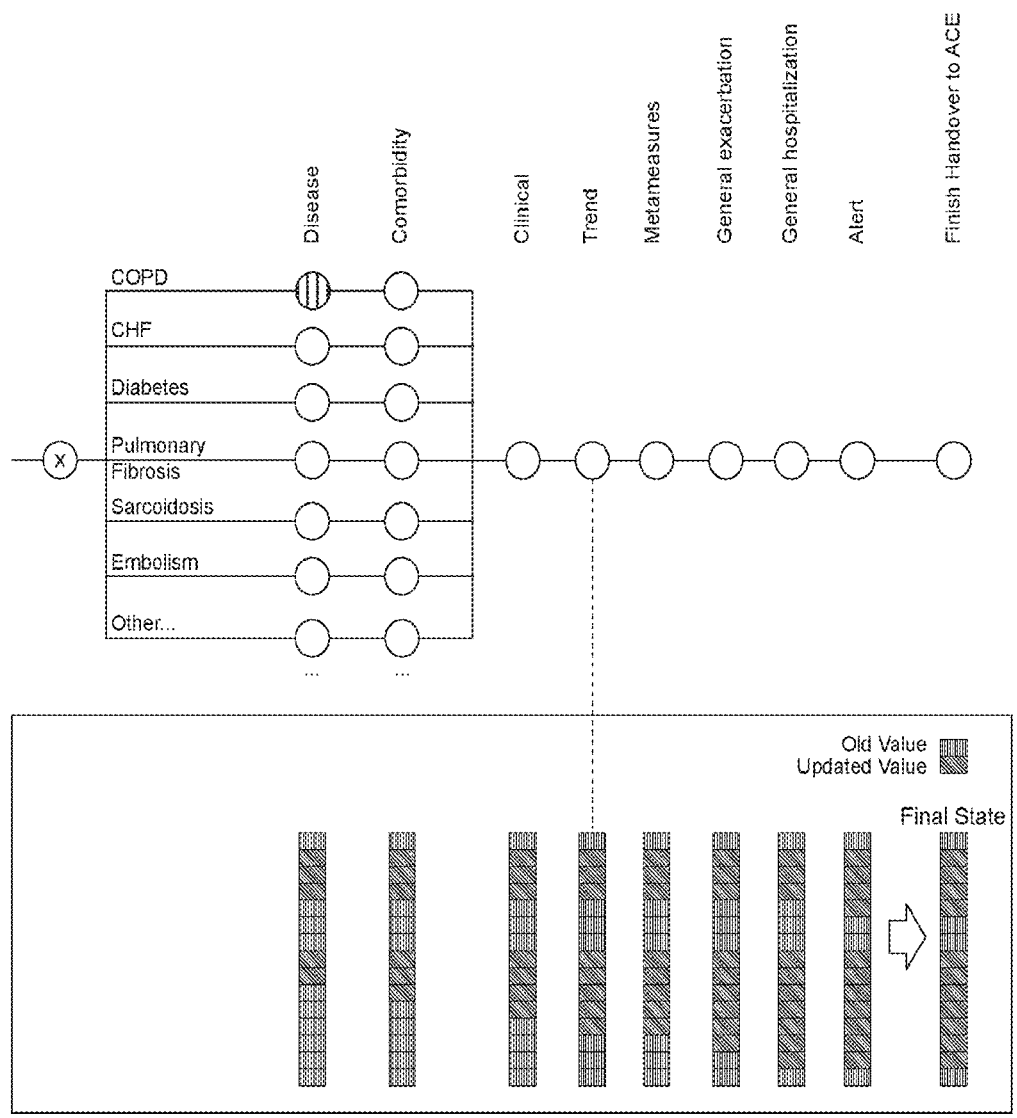
Figure 7:
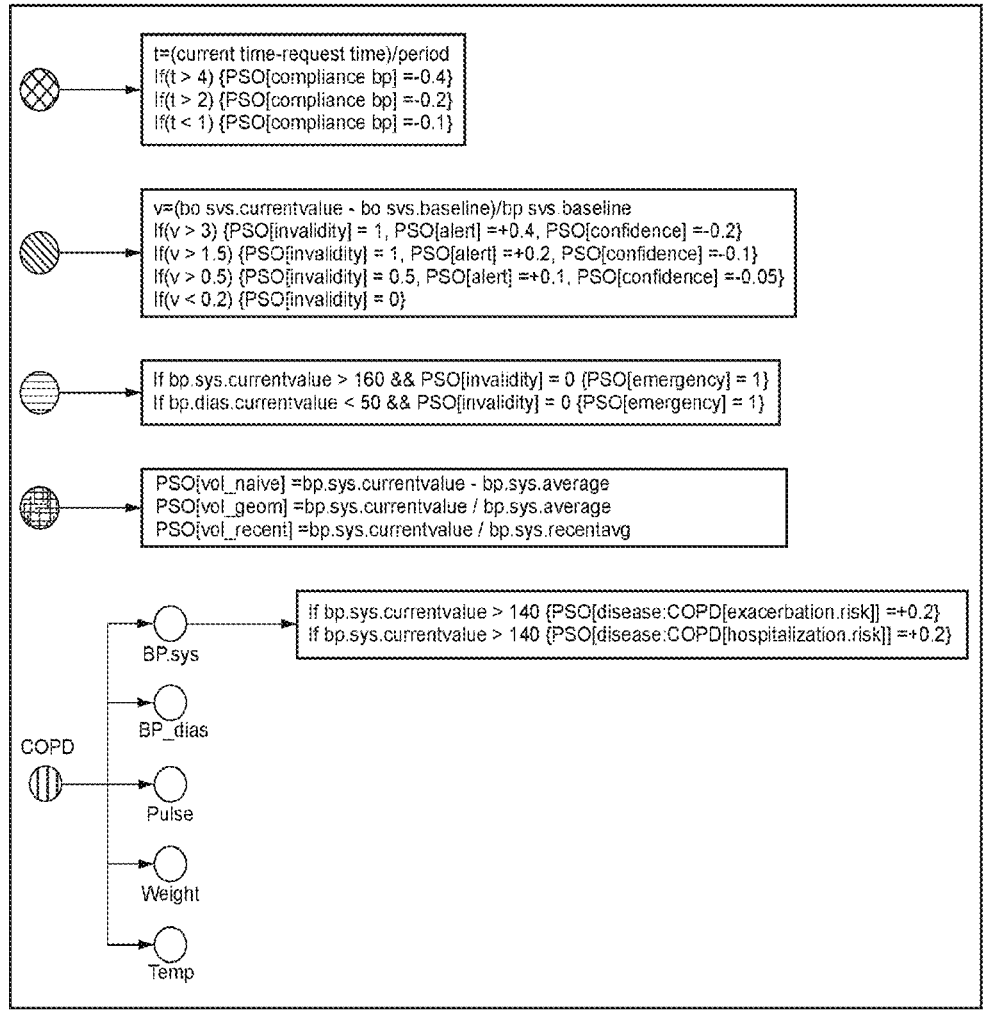
FIG. 7 illustrates logic which could be used by a state controller engine to make changes to a patient state object.
Figure 8:
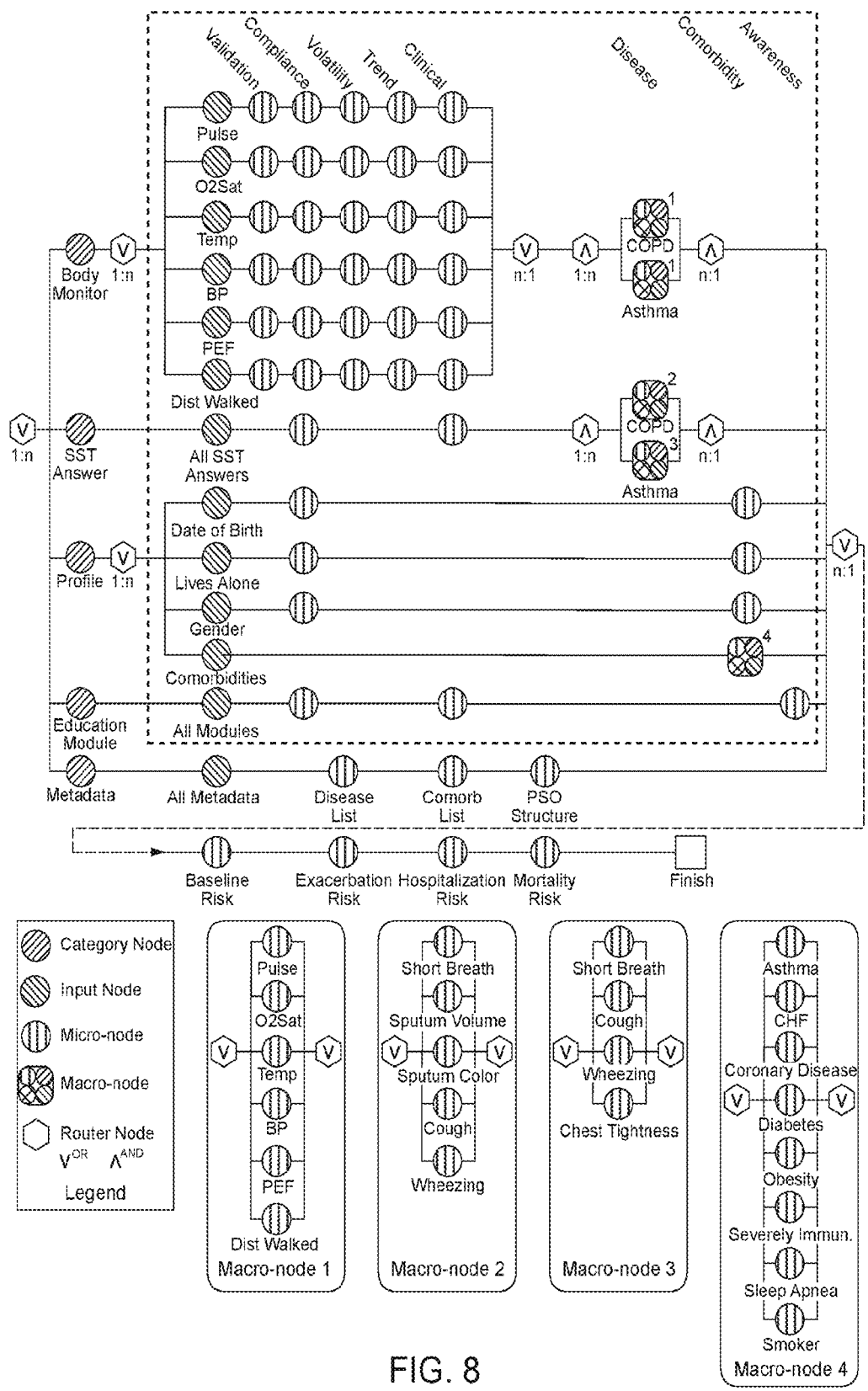
FIG. 8 illustrates at a high level certain logic nodes which could be included in some embodiments which implement a state controller engine.

Turning now to FIG. 5's state controller engine (SCE) 502, that element could be implemented as a module containing a set of rules which would be invoked when a data item about a patient is captured to determine whether and how the PSO 501 should be updated. In a system implemented using the architecture of FIG. 5, there could potentially be only a single state controller engine 502 which would be used for controlling updates to patient state objects 501 for all patients. Such a SCE 502 could be implemented by starting with a few basic rules, and continuing to add new rules over time to make the SCE 502 more intelligent. An SCE 502 will preferably have access to all raw data for a patient, as well as access to the current PSO 501 and all past states of the PSO 501. In practice, a SCE 502 will likely to implemented to generally look at only the latest piece of data about a patient and use it when updating a PSO 501. However, it is possible that an SCE 502 may also choose to look at some other patient data when formulating an update. Such an update could be triggered in a variety of ways, and there could be multiple ways of triggering an update implemented even within a single embodiment. For example, it is possible that a single implementation may include an SCE 502 which would be fired in one of two ways: either when data is updated for a patient a message could be passed (e.g., by a DCE 504, discussed infra) to the SCE 502 causing it to fire, or the SCE 502 could collect historical data on a regular schedule and update a patient state object 501 accordingly. FIGS. 6A and 6B (in which FIGS. 6A and 6B form a single drawing when the right side of FIG. 6B is placed adjacent to the left side of FIG. 6A) illustrate how a SCE 502 could update a PSO 501. FIG. 7 illustrates logic which could be used by a SCE 502 to make changes to a PSO 501 at various points shown in FIGS. 6A and 6B. FIG. 8 illustrates at a high level certain logic nodes which could be included in some embodiments which implement an SCE 502 such as illustrated in FIG. 5.

Turning now to FIG. 5's action controller engine (ACE) 503, in an embodiment following FIG. 5, the action controller engine 503 may be called when a PSO 501 is updated by a SCE 502. The ACE 503 may then evaluate rules using data from the PSO 501 to determine what (if any) action(s) should be taken as a result of the update. Similarly, in some cases an ACE 503 may also include rules which are run on batch processes triggered by a clock based on time, rather than being triggered by an update to a PSO 501. Actions which could be triggered by an ACE 503 could include any actions the individual or entity operating the system in which that ACE 503 is present chooses. For example, such actions could involve communication with a patient, HCP, or caregiver computer. Such actions might include, for example, requesting health data from the patient, requesting an update to a body monitor measurement, providing recommendations to the patient (e.g., recommending that the patient seek medical attention, recommending that the patient take particular medications, etc.), providing notifications to one or more of the patient's HCPs or caregivers (e.g., notifying a HCP or caregiver of the patient's state or of a change in the patient's state), triggering an SST, sending a reminder to the patient, or issuing an instruction to a patient (e.g., call 911, call a doctor), to name a few. Actions triggered by an update in the PSO 501 could include altering the frequency or timing with which particular health data is collected and/or causing the collection of additional or different health data from the patient.

In some embodiments, the rules that an ACE 503 could use to trigger actions could read a patient state representation and, based on the risk and state scores, determine whether certain actions should be triggered automatically. Actions that could be triggered by rules based on a patient state representation could include, e.g., providing recommendations and/or notifications to a patient, health care provider, or caregiver. Additionally, actions that could be triggered include those affecting the system, e.g., causing changes in behaviors of the system. Behaviors of the system could include, e.g., interactions with users, e.g., patients and/or HCPs. For example, actions could include altering the frequency at which the system requests data from a patient or from a monitoring device and/or resetting a time associated with data which would be requested from a patient or from a monitoring device. One or more rules could be invoked upon an update in the patient state representation. A given rule might trigger one or more additional rules.

Alternatively or additionally, an action controller engine 503 might have one or more rules that specify situations in which an SST should be executed, rules that specify which among multiple different SSTs to execute under specified circumstances, or both. For example, an action controller engine 503 might have rule(s) that cause an SST to be executed upon receipt of an abnormal value of a physiological variable, rules that specify which SST to execute given a normal value of a physiological variable, or both. Thus, while, in some embodiments which utilize the architecture of FIG. 5 an outcome (e.g., a measurement which may be, but would not necessarily be, a reflection of the ultimate result of a course of treatment) could be a data point which would not itself trigger any action in the regular course of operation, such outcomes could be evaluated by an SCE 502 to determine if they are in a range of concern. If an outcome is such that it triggers a smart symptom tracker (SST), the outcome becomes a "Sign." Once an outcome becomes a sign, and a sign triggers an SST, the SST asks the patient various questions which are related to symptoms. Signs will typically be dynamically determined, and such determination will preferably be based on dynamic processing rather than hardcoded linear rules, such that rules encoded in an SCE 502 will leverage a PSO 501 to dynamically determine if an outcome qualifies as a sign. Through leveraging a back end architecture such as shown in FIG. 5, such rules may look into multiple aspects of a patient's health data and determine if a given outcome reading qualifies as a sign. Of course, it is possible that, in some embodiments, not all outcomes will be processed in order to determine if they qualify as signs. For example, some embodiments may be implemented to prevent physician reported outcomes from triggering SSTs, in which case it might simply be impossible for a physician reported outcome to be treated as a "Sign." It is also possible that, in some embodiments, signs could be used for purposes other than triggering SSTs, such as serving as data markers for studies and analytics. For example, signs linked to particular potential causative factors may be used for data analysis (e.g., to find relations and causations).

Other rules related to SSTs might also be presented various embodiments following the architecture of FIG. 5. For example, in some such embodiments an action controller engine 503 might have rules that assemble an SST by, for example, selecting appropriate (as determined by the rules) data requests from a set of data requests. Such an SST may be referred to as a "virtual" SST. The content of such an SST (e.g., data requests included in it, instructions issued by it) could be determined based on the patient's state at the time. The content of a virtual SST could vary depending on, e.g., individual patient characteristics (e.g., risk level, comorbidities), which could be included among the data in the patient state object for that patient or could be stored in a patient record in the database and used by the SST. When asking questions from a virtual SST, the answer to each question in the virtual SST session could be treated as if it were completely independent of every other question, and the answers to the questions could be run through the SCE 502, which would make updates to the PSO 501. Control would then be handed back to the ACE 503, which could read the PSO 501 to determine which questions/instructions should be provided to the patient.

In embodiments where the virtual SST concept is implemented, a virtual SST session could be triggered by body monitor readings. For example, if a body monitor reading is in a certain range, a node in the SCE 502 could trigger a VSST session by setting a VSST session in the PSO 501. The node in the SCE 502 could also turn on the questions in a global questions array (discussed infra) for the patient for whom the VSST session would take place. Once the VSST session has been triggered, control could be handed over to the ACE 503, and a dedicated "super rule" in the ACE 503 dedicated to running a VSST session could be fired. This node in the ACE 503 could read the PSO 501 and see that the VSST flag is set to ON. In response, it could go to the global questions array, find the questions for that patient, check which questions are on, and send the first question which is ON for that patient to him or her by adding it to the ICE 507 schedule (discussed infra) with an immediate timestamp. After a question has been asked, it can be marked as asked for that patient, and switched off of a pending questions list. When the answers to the questions come back, they can be run through the SCE 502 nodes dedicated to the given SST questions. The logic in these nodes can update PSO 501 scores. They can also trigger new questions to be switched on in the Global Questions Array for the patient. They can also switch on medication instructions in the Global Instructions array. An instructions issuing node in the ACE 503, may prevent any instructions from the Global Instructions Array from being sent to the patient, until the VSST session is over (flag in PSO 501 is set to OFF). Once the session is over, the instructions issuing node can review the instructions switched ON in the global instructions array, and check if there are conflicts. If there are conflicts, it removes them, and then sends the ON instructions out to the patient.

Of course, it should be noted that, in some embodiments, an instructions issuing node in an ACE 503 could also be utilized outside of the context of a VSST session. If there is no VSST session on, but a new datapoint comes in (e.g., a body monitor answer), that may also trigger instructions in the Global Instructions List to be turned ON. In this case, when control passes to the Instructions Issuing Node in the ACE 503, it will simply push the instructions out. Similarly, just as an instructions issuing node could potentially be used both inside and outside of the context of a VSST session, it is also possible that, in some embodiments, data other than that collected in a VSST session could be used in determining recommendations determining when to trigger an SST, and/or determining the content of an SST. For example, other data that could be contained in the patient's PSO 501, e.g., data such as the patient's age, overall health status, other conditions, risk levels, etc., could be used for such purposes. Further, SSTs could be specialized for particular purposes. For example, certain SSTs could be designed for following up with a patient after the system provided a recommendation or detected a trend of concern. Follow-up provided by a system (whether through SSTs or otherwise) could be designed to collect data allowing the system to determine whether the patient had followed the recommendation, had improved or worsened, whether additional recommendations are warranted, etc., and could include the provision of additional recommendations based on analysis of the data collected during the follow-up and, in some instances, data collected previously by the system.

Figure 9:
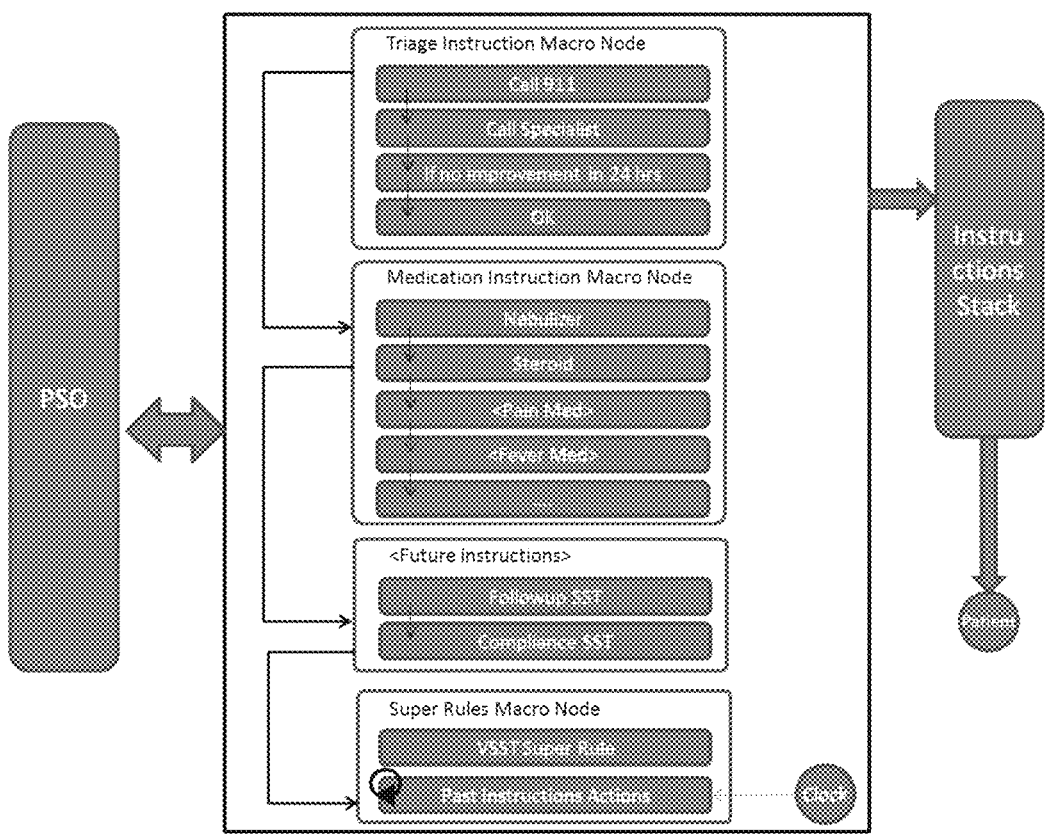
FIG. 9 illustrates an architecture which could be used to implement an action controller engine.
Figure 10:
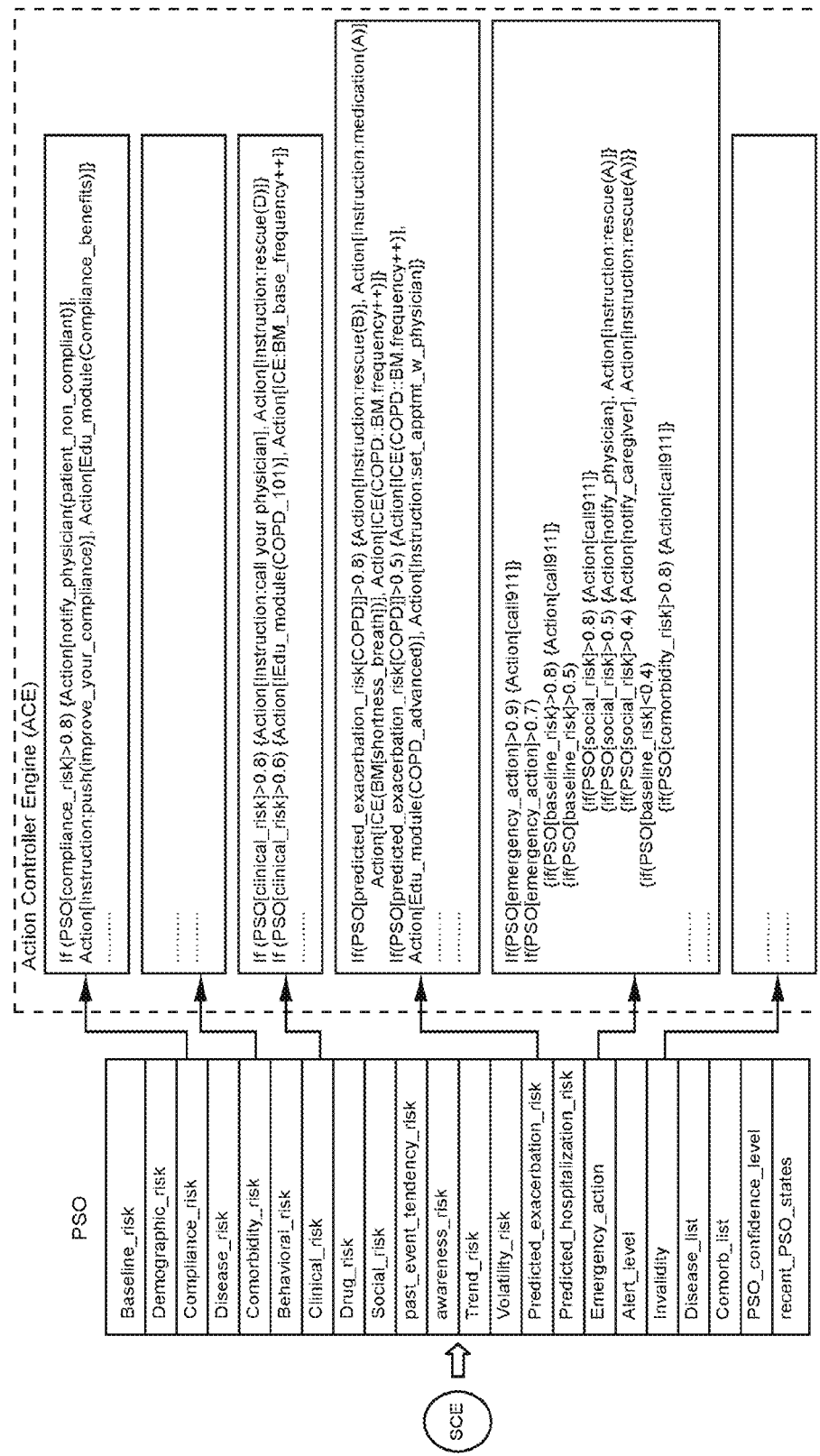
FIG. 10 provides certain details regarding particular types of evaluations which could be performed by an action controller engine.

A diagram of an architecture which could be used to implement an ACE 503 is provided in FIG. 9, with FIG. 10 providing more details of particular types of evaluations which could be made by such an ACE 503. In an ACE 503 implemented as shown in FIG. 9, each macro node could be dedicated to a certain type of rules, and each micro node could have one possible output instruction. Within a macro node, the micro nodes could be run in an order set based on their priority, and once each micro node in a macro node has been run, execution could move to the next macro node so that the micro nodes in that macro node could be run as well. As shown in FIG. 9, each node could potentially create an instruction, which could be placed on a stack, though in some embodiments instructions may not be sent out till ACE 503 completes its processing. In such embodiments, once ACE 503 completes its processing, instructions from the stack are sent to patient. This may be done directly, or, in some embodiments, another check might be performed before the instructions are sent out. Of course, it should be understood that other architectures than a macro node/micro node architecture such as shown in FIG. 9 could also be used when implementing an ACE 503. For example, in some cases, rather than organizing rules into macro and micro nodes as described, rules could be organized into a single type of nodes, such as nodes based on subject matter (e.g., nodes with rules used for processing temperature data). In such a case, when an ACE 503 was triggered to process information from a PSO 501, the ACE 503 could take the information to be processed (e.g., information updated by an SCE 502) and provide it to the relevant nodes (e.g., if the information to be processed is temperature information, it could use a data structure such as an index to identify the temperature specific nodes and nodes with rules for generic body monitors, and then provide the information to those nodes) so that they could evaluate it and generate whatever instructions (e.g., output instructions, modifying the PSO 501, triggering other rules or nodes, etc) their rules indicated were appropriate. In such a case, node sequencing could be controlled by an execution order parameter specified as part of the definitions of the relevant nodes, and separate sequencing and organization on macro and micro node levels could be omitted. Accordingly, the discussion of the macro/micro node architecture from FIG. 9 should be understood as being illustrative only, and should not be treated as limiting on the protection provided by this or any related document.

Taken together, a PSO 501, an SCE 502 and an ACE 503 can be conceptualized as a three level architecture for converting input data about a person into a holistic representation of a patient's health state which can be used as basis for further action. The first level (SCE 502) converts raw data (e.g., values of physiological variables, patient responses to questions about symptoms) to a patient state representation (the PSO 501). The second level is the patient state representation (PSO 501) which can be represented in the form of a numerical score assignment to various aspects of (or related to) a patient's health. The third level (ACE 503) is the reading of the patient state representation to trigger health actions which can be used in managing a patient's health, e.g., for purposes of improving/maintaining patient health and/or improving health outcomes. The three levels could run without human intervention based on rules embedded in the system. Input data could be a combination of any one or more of the following: answers to questions about physiological variables (e.g., requests to the patient to enter and measure such variables), answers to symptom questions, data from monitoring devices, patient profile data (e.g., patient characteristics such as risk factors or behavior patterns that can affect health), patient disease data (e.g., which conditions a patient has, their severity, or other relevant information), patient demographic data, patient social data, and other possible data sources such as those discussed herein. Input data about a person, as used herein, could include data about such person's environment (physical, social). A patient state representation can be created by converting raw medical data into a scoring model, where raw data is used to calculate or refine a risk or state score for the patient. The mapping of raw data to risk data could be done by a variety of approaches. For example, a combination of medical research interpretation (e.g., analysis of studies reported in the medical literature) and learning models which take historical patient raw data and final outcomes data to derive appropriate scoring regimes could be used. A system implementing the disclosed technology could evolve over time from one that utilizes primarily scoring models derived from analysis of the medical literature to one that utilizes scoring models derived from the raw data and outcome data gathered by the system. An example of medical research that could be used in deriving a scoring model would be studies that have examined factors associated with mortality, hospitalization, hospital readmission, or health care utilization of or by patients with particular conditions.

Advantages, some or all of which could be provided by various embodiments implemented using an architecture such as shown in FIG. 5 with a PSO 501, SCE 502 and ACE 503 as described herein include the following:

1) A patient state object 501 may provide a complete holistic view of patient at all times.

2) Data feeds ramifications into one place—which can facilitate making decisions and taking actions based on complete information about patient health 3) Very sophisticated decision logic can be implemented for actions. E.g.: When asking patient to call 911, it is possible to look at answers to subjective questions, recent BM measurements, volatility in BM measurements, recent trends in BM measurements, prior patient risk level of exacerbation for given disease, patient general risk level which is influenced by comorbidities and so on. For example, a patient who has low risk based on subjective questions but high general risk level due to comorbidities, will get 911 much faster than someone who has very low general risk level due to lack of comorbidities. This could provide for more powerful analysis than would be generally be available by focusing on SST questions alone.

4) The concept of a virtual software model of the patient is powerful and allows for high level of extensibility.

5) This model largely separates data capture, data interpretation and decision logic, which allows maximum modularity.

6) Any decisions made regarding a patient (trigger SST, ask for BM, issue action/instruction, notify physician etc.) can be done from a single object. Decision logic can be localized in one place, allowing easy updating, easy adding of new rules, logic and actions 7) It could be possible to add any new rule into an existing system, since it will be part of the SCE 502 or ACE 503. SSTs, BMs etc may not require modification to add such new rules, but instead might be treated as naked sensors, with no intelligence of their own.

8) It could be possible to evolve ACE 503 and SCE 502 over time and AI technologies can be applied here, in a very clean and elegant way 9) Every feature added in the future that may understand patient state may not be required to query any object other than the PSO 501. This could avoid the necessity of having to go to n different data points to make a decision. Accordingly, a decision can be made simply from looking at some component of PSO 501.

10) The architecture allows for separation of interaction modules (BM, SST etc) from knowledge modules (rules from medical team) from learning modules (how to update patient state object based on incoming data, to best reflect TRUE patient state). Each can be developed and modified independently.

Moving beyond the PSO 501, SCE 502, and ACE 503, FIG. 5 also depicts a patient interface object (PIO) 505, which can be implemented as a data structure which reflects the merged and optimized specifications of interaction modules that interact with the patient. Such a PIO 505 could define information for a patient such as what SSTs will run, which body monitors (BMs) will run, what educational modules are relevant for a given patient, what sensors the patient interacts with, at what frequencies data is captured, what channels data is captured from etc, and may also include data for controlling the frequencies and expiration of these elements. Preferably, each patient for whom information is managed by a system following the architecture of FIG. 5 will have his or her own patient interface object 505, allowing the patient's specific PIO 505 to be updated as necessary as new data sources are added for him or her.

To illustrate the type of information which could be maintained by a PIO 505, in some embodiments, a PIO 505 could include:

Which DCM's (i.e., Data Capture Modules, a phrase used in this document to refer to Revon application modules which get data about a patient, from the patient or elsewhere) to run for this patient;

When to run each DCM;

What is the D-plan parentage of each DCM, which can be relevant when a D-Plan is changed or removed.

Such a PIO 505 can be implemented as a graph data structure or a simple multidimensional vector, an example of which is presented below in table 2.

TABLE 2

Exemplary Patient Interface Object

PIO(patient_k) = {
    [tplan1[(SST: SST_copd(24), SST_asthma(72))(BM: bp_BM(48), pulse_BM(48), weight_BM(96))(Edu: copd_101, asthma_101, smoking_cess)]]
    [tplan2[(SST: SST_asthma(48), SST_diabetes(96))(BM: bp_BM(24), pulse_BM( )48), sugar_BM(24))(Edu: asthma_101 smoking_cess, diabetes_101)]]
    [merged_DCM[(SST: SST_copd(24), SST_asthma(48), SST_diabetes(96))(BM: bp_BM(24), pulse_BM(48), weight_BM(96), sugar_BM(24))(Edu: copd_101, asthma_101, smoking_cess, diabetes_101)]]
}

Figure 13:
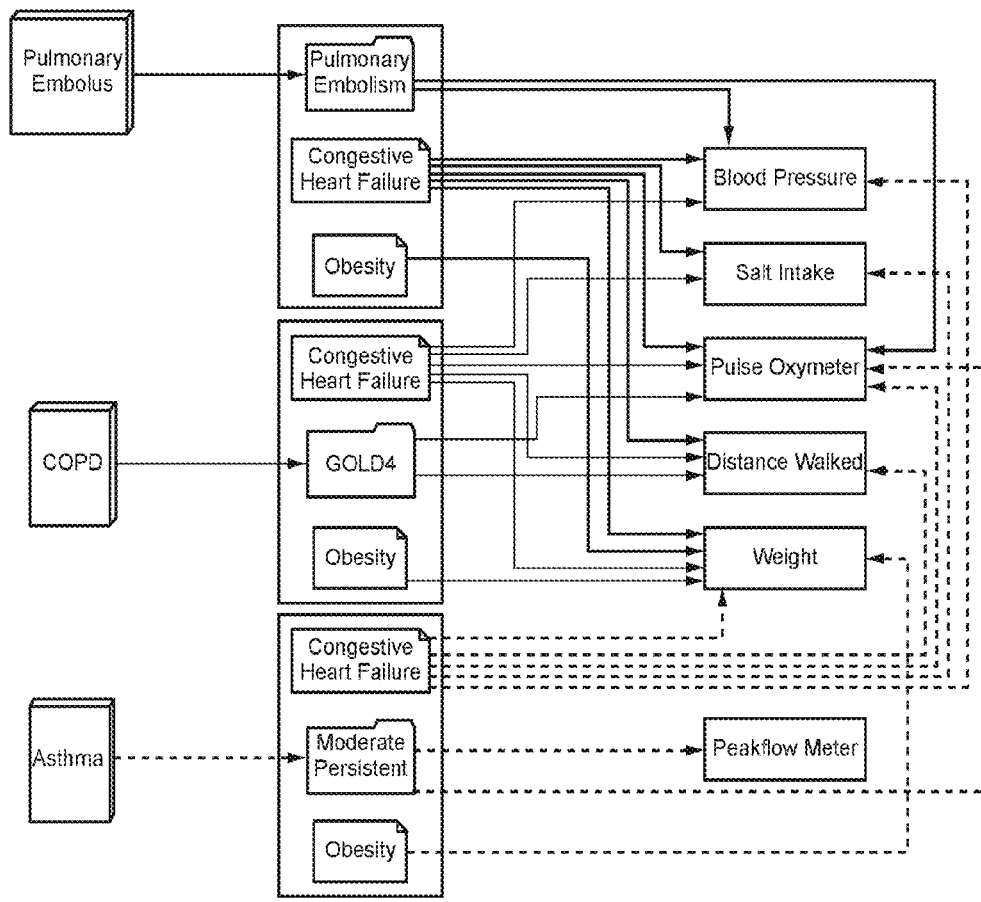
FIG. 13 illustrates a patient interface object organized into a three level graph.

An illustration of a PIO 505 organized into a three level graph (with the levels corresponding to a D-plan family, a D-plan, and body monitor modules) is provided in FIG. 13. In that figure, as D-plans are added to a patient profile, the IDE 506 adds vertices to the PIO graph. When doctors turn on/off modules in a D-plan, the IDE 506 responds by adding or removing edges or vertices from the graph.

Moving on from the PIO 505, FIG. 5 also illustrates an interface design engine (IDE) 506, which can perform actions such as taking D-plan specifications from the physician and determining which SSTs, which BMs and which Edu modules (potentially including medications, procedures, etc) to run for the patient. In some implementations, an IDE 506 could also determine how to merge and de-merge SSTs, BMs and Edu modules, and create the Data Capture Sensor Pool (DCSP) for the patient, which reflects the final merged and optimized set of SSTs, BMs and other data capture components. Preferably, as D-Plans are updated by physicians, new ones added, old ones removed, comorbidities changed and so on, the IDE 506 will update the patient's PIO 505 to reflect the current active set of Data Capture Modules. A system implemented according to the architecture of FIG. 5 could include only a single IDE 506, which would update all PIOs 505, with each patient having his or her own PIO 505. The IDE 506 will take as input the physician specifications of D-plans for a given patient. With this input, it will create the PIO 505 data structure. When physicians update (or add, delete) D-plans, the IDE 506 will update the patient's PIO 505 accordingly. An IDE 506 takes as inputs the D-Plans assigned to the patient by the physicians. It translates the D-Plans into a set of DCMs, such as SST's, Body Monitors and Education Modules that interact with the patient. This can be useful because multiple D-Plans can have an overlap in the data capture modules they contain. They can also have a conflict, where the same DCM prescribed has some differing characteristic such as frequency. However, as far as the patient is concerned, there can be only one unique manifestation of each DCM. The IDE 506 is therefore tasked with merging and demerging different D-Plans and having the D-Plan changes reflect in the PIO 505. The IDE's 506 output is writing and editing the PIO for a given patient.

Preferably, in operation, an IDE will execute the following rules:

1) If a new D-plan is added, it checks what BM, SST and Edu modules this D-Plan adds. It then checks if any of the BM, SST or Edu modules are already active for the patient from an earlier D-plan.
2) If, for a given DCM such as a BM, there is no existing requirement, the IDE 506 will add that BM by writing it into the patient's PIO 505.
3) If a given DCM, such as a BM or SST, is already in the patient's PIO 505, it checks if the new D-plan's specifications for the given DCM are different from the existing specification (e.g., the DCM's frequencies and alert level).
4) If the specifications are the same, it does nothing, as the DCM is already active for the patient. If the specifications are different, it selects the higher 'strength' specifications and rewrites the PIO 505 to change the DCM specifications to the stronger (e.g., higher alert level and/or higher frequency) specifications from the new D-plan.
5) When a D-plan is removed, the IDE 506 checks which all DCMs this D-plan imported into the patient's PIO 505. For each DCM imported into the PIO 505 by this D-plan, it checks if that DCM is also applicable to any other active D-plan. If not, the DCM is switched off. If the DCM is applicable to another D-plan, the IDE 506 checks if this D-plan's specifications for the DCM are stronger or weaker. If weaker, it makes no change. If stronger, it checks other D-plans, and downgrades the DCM's specifications to the next strongest specifications.

For the purpose of implementing these rules, it should be understood that when a DCM is added, whether Body Monitor or SST, each will preferably come with 3 frequency levels—High, Medium, Low. Based on the alert level set for the DCM, one of the frequencies will be used. The frequency will be set by default in the D-plan, but the physician can reset the frequency up/down by changing the alert level. It should also be understood that there could be a separate patient alert level, which would be specified in the PIO 505. In some embodiments, such a patient alert level could be limited to two states—High and Normal. In such an embodiment, if the patient alert level is Normal, the system would simply use the individual alert levels for each DCM to select the frequency. Alternatively, if the patient alert level is set to high, the system would use the highest alert level for each DCM. A list of exemplary interactions a doctor could have with an app front end in some embodiments which could cause a message to be posted to an IDE 506 and the IDE 506 to update a PIO 505 to track the modified D-plan are set forth below in table 3.

TABLE 3

Exemplary actions which could trigger a message to an IDE.

Add a D-plan
Add comorbidities (these may actually be imported from the patient profile, which the doctor may modify)
Turn SSTs on/off
Turn monitors on/off
Turn education modules on/off
Change the frequency of any of the above 3

TABLE 3-continued

Exemplary actions which could trigger a message to an IDE.

Remove a D-plan
Remove comorbidities from the patient profile

In addition to the IDE 506, the architecture of FIG. 5 also includes an interface controller engine (ICE) 507. The Interface Controller Engine 507 reads the PIO 505 to understand what actions should be taken with respect to the patient (e.g., app initiated requests for data). Accordingly, it is possible to conceive of the PIO 505 as functioning as an instruction sheet for the ICE 507 to follow. Based on the PIO 505, the ICE 507 will know which SST, BM or other modules to run and when, for any given patient. The ICE 507 reads the PIO 505 of a patient and figures out what actions to schedule, and could potentially maintain a local database of patient requests for data so that it can autonomously schedule and post such requests. It converts data from the PIO 505 into a queue of actions with appropriate times for the actions (e.g., figuring out which BM requests to send and/or which SST requests (if any) to send). In some embodiments, an ICE 507 could also be implemented to track when a request is not filled, and if to run a follow up to get the data from the patient. When the patient responds (e.g., by entering data into an app), the ICE 507 gets the data back and passes it (either directly or after performing some level of validation on it) to the DCE 504 to store and process. To facilitate this, the ICE 507 could be configured with an inventory of actions (e.g., notifications) available to it. Using the PIO 505, it selects from this inventory of actions, and puts them on a queue for delivery to the patient, with ideal delivery times. The messages may then go to the Engagement Engine (EE) 508 (discussed infra) or could be sent directly to the patient via an application front end or to other appropriate endpoint (e.g., a BM), depending on the embodiment and the context in which it is deployed.

Conceptually, some embodiments of an ICE 507 can be seen as responding to four types of events. Those types events, as well as actions which could be performed on incoming user data, are described below:

Administrative:
   Responds to "new patient" message from PIO. Updates local database of schedule requests
   Responds to "change patient alert state" from ACE. Updates local database, based on PIO App-Initiated, Scheduled:
   Maintains local database of all some or all requests to make to patients
   posts requests to EE as scheduled, based on database
   once a request is posted, the database is updated and request scheduled for next time, based on frequency
   when patient responds to request, ICE asynchronously sends response to DCE App-Initiated, Unscheduled:
   receives request from ACE for information
   request immediately appears on app front end as a dialog box, page, etc
   patient response collected by ICE and sent to DCE User-Initiated:
   User may volunteer to enter data at any time
   ICE receives any new data and posts to DCE All User Data:
   May be filtered by ICE for basic out-of-range. If so, user is immediately asked for new data. (there could be a handshake protocol between app front end and ICE for this)
   Results in an update to the ICE scheduling database. ICE searches for the next scheduled collection point of received data and changes the next scheduled time, based on prescribed frequency Another way of conceptualizing the role an ICE may play in interactions with patients in some embodiments is as performing the following four functions:

1) The ICE 507 schedules and sends to the patient the following types of data
   Questions to ask the patient from an SST session, now
   Instructions to issue the patient, now
   Scheduled notifications to send, based on T-plan frequencies, at a future time
   Follow-up questions from body monitors 2) The ICE 507 processes and sends to the DCE 504 the following patient input
   Answers to immediate questions
   Answers to scheduled notifications
   Unprompted data input 3) The ICE 507 is responsible for maintaining metadata on patient input
   Where the input comes from (SST, unprompted, prompted, etc.)
   Timestamp
   Type of input (monitor, symptom, profile, etc.)
   Was the data on time, or expired (if prompted?)

4) The ICE 507 maintains, at all times, a schedule of upcoming notifications to send including, time to send, time of expiry and scheduled frequency, for each notification.

It should be noted that, while the above discussion focused on scheduled actions based on information from a PIO 505, in some embodiments, an ICE 507 could handle unscheduled actions and/or actions based on information from other components of the system. For example, in some embodiments, an ICE 507 could handle direct requests from an ACE 503, such as to send data requests to a patient. These interactions could be scheduled interactions (which would likely be the case in an embodiment in which an ACE was configured to handle unscheduled interactions through another component, such as directly through an EE 508), or could be unscheduled interactions as well. For example, in some embodiments, an ACE 503 could send an ICE 507 instructions to trigger actions such as sending a BM question or SST question out of schedule. An exemplary output packet for communicating data from an ACE 503 to an ICE 507 is provided below in table 4.

TABLE 4

Exemplary data packet from ACE to ICE packetID
patientID
Timestamp
Type - instruction, question, scheduled notification
Content - text of message, etc.
ScheduledDeliveryTime - either NOW or future date
Duration - time until expiration
Frequency - how long until resend (not always used)

Figure 11:
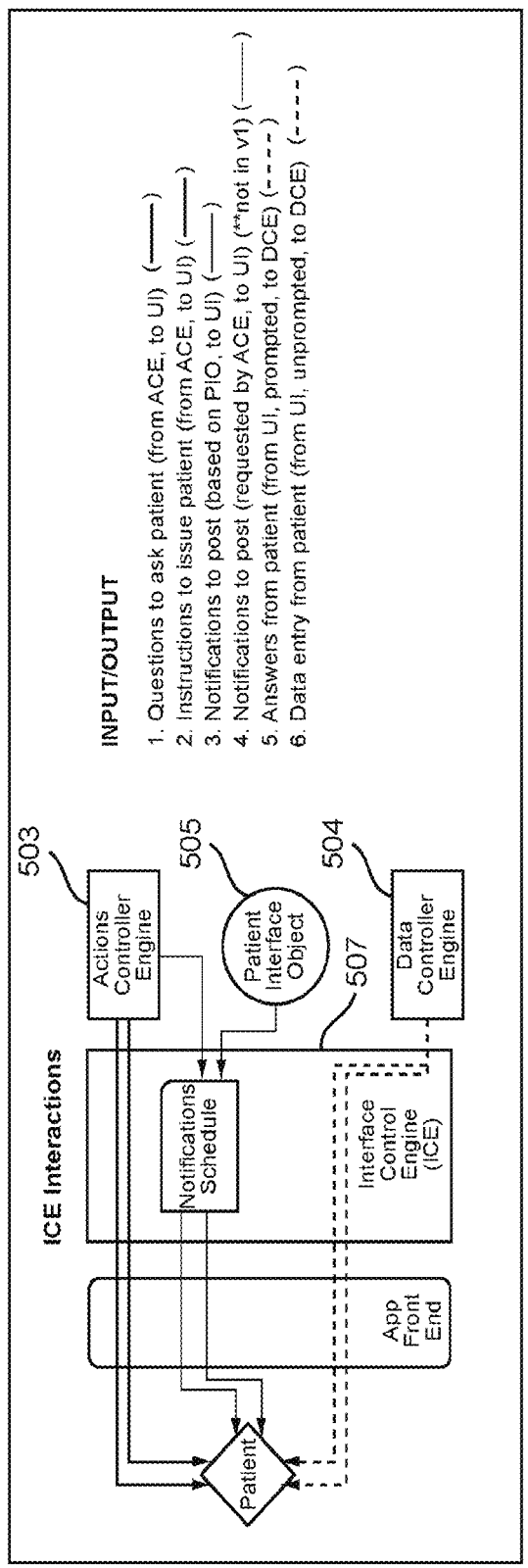
FIG. 11 provides a high level chart of data flows which could take place in some implementations of the disclosed technology.
Figure 12:
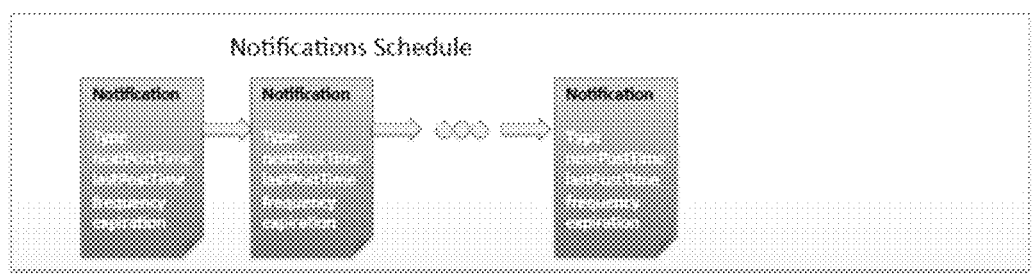
FIG. 12 illustrates how a notifications schedule from an interface controller engine could be represented.

FIG. 11 provides a high level chart of data flows which could be involved in this process, as well as data flows from the PIO 505 through an ICE 507 to a patient and from the patient through the ICE 507 to a DCE 504. FIG. 12 illustrates how a notifications schedule from an ICE 507 such as shown in FIG. 11 could be represented.

The final element illustrated in FIG. 5 for interacting with a patient is the engagement engine 508. As set forth above, an engagement engine 508 may deliver messages provided to it from an ICE 507. Such delivery could take place at a time requested by an ICE 507, or could be at another time if the EE 508 feels the need to modify it. While the architecture of FIG. 5 may be implemented without an engagement engine 508 separate from the ICE 507, in embodiments where it is present, the EE 508 will control delivery of messages to users, mainly patients. This can take place with the EE 508 being called by the ICE 507, and receiving a current scheduled list of notifications, to send the patient, reorders the list as necessary by rescheduling events, and sends the list back to the ICE 507. In embodiments where this takes place, there could be a parallel process for questions/instructions to be asked/executed "now", which the ICE 507 could filter out before sending a list of notification to the EE 508 and processing directly itself. Similarly, it is possible that an EE 508 could read an array/list of output packet objects (e.g., objects including data such as shown in table 4) maintained by the ICE 507, and reschedule them by updating a ScheduledDeliveryTime element in the header of a packet, effectively resetting the scheduling of the corresponding notification. In some embodiments it may not generate messages (which function could be performed by ACE 503), but it controls when and how the messages get delivered, to maximize the engagement of the user and optimize the user experience. In some embodiments, there may be only one engagement engine 508 across the application.

The final group of item illustrated in FIG. 5, the data controller engine (DCE) 504 and patient data object (PDO) 509 may be used to control the data available to an entity operating a system implemented according to the architecture of FIG. 5 (e.g., by controlling where data captured by an ICE 507 is stored). These modules may also provide a simple intelligent interface for other modules to request raw patient data. The PDO 509+DCE 504 can control storage and access to raw patient data, while the PSO 501 uses this raw data to provide a summary view of the current patient state, calculating various measures based on this raw data. Each of the data controller engine 504 and patient data object 509 is discussed in more detail below.

Turning first to the patient data object 509, in some embodiments, that item could be implemented as a simple data structure which represents a map of data items collected about a patient and where they are stored (e.g., an XML file that describes what data is collected for a patient and maintains metadata about this data). Each patient will preferably have his own PDO 509, which reflects the list of sources of data used for that patient. In effect, the PDO 509 says what data we are collecting for a given patient. In some cases, such as where the only source of data for a patient is what is specified in D-plans, the PDO 509 and PIO 505 for a patient will likely hold substantially the same information about a patient. However, if there are additional sources of data (e.g., non-D-plan sources of data), then these will preferably be reflected in the PDO, but not included in the PIO 505 as well.

Preferably, the PDO 509 will not store raw data, but instead will only keep a map of what data is collected and, in some cases, where it is stored. The State Controller Engine (SCE) 502 will read the PDO 509 to figure out what data is being collected for a patient, and collect that data from the relevant datastore itself for any scheduled updates to the PSO 501. In some embodiments, other services may also use the PDO 509 to figure out what data is available for a given patient. An illustrative example of a data structure which could be used to implement a PDO 509 is provided below in table 5.

TABLE 5

Exemplary patient data object data structure

```
<PDO>
  <PatientID>192863</PatientID>
  <DateCreated>201404101110</DateCreated>
  <DCM>
    <BM>
      {Blood_Pressure, Internal, Float_regular, S3, PHI, {SCE},
      201406201238, None}
    </BM>
    <BM>
      {Temperature, Internal, Float_regular, S3, PHI, {SCE}, 201406201238,
      None}
    </BM>
    <BM>
      {Weight, Internal, Float_regular, S3, PHI, {SCE}, 201406201238, None}
    </BM>
    <BM>
      {Distance_walked, Internal, Float_regular, S3, PHI, {SCE},
      201406201238, None}
    </BM>
    <SST>
      {Shortness_breath, Internal, Int_regular, S3, PHI, {SCE}, 201406201238,
      None}
    </SST>
    <SST>
      {Wheezing, Internal, Int_regular, S3, PHI, {SCE}, 201406201238, None}
    </SST>
    <SST>
      {sputum-color, Internal, Int_regular, S3, PHI, {SCE}, 201406201238,
      None}
    </SST>
    <SST>
      {sputum-volume, Internal, Int_regular, S3, PHI, {SCE}, 201406201238,
      None}
```

TABLE 5-continued

Exemplary patient data object data structure

```
    </SST>
    <SST>
      {chest-pain, Internal, Int_regular, S3, PHI, {SCE}, 201406201238, None}
    </SST>
    <Payer_records>
      <Provider_name>BCBSKY-Horizon</Provider_name>
      <Provider_ID>1234</Provider_ID>
      <Provider_data_elements>
        {Policy-Info, External, JSON, S3, PHI, {SCE}, 20140101045,
          None}
        {Events, External, JSON, S3, PHI, {SCE}, 20140101045, None}
      </Provider_data_elements>
    </Payer_records>
  </DCM>
</PDO>
```

As stated previously, the PDO 509 will preferably not store raw data. Instead, raw data coming from an ICE 507 or other data source 510 will be taken and stored in a datastore 511 by DCE 504. The DCE 504 which may then update the PDO 509 if necessary to reflect where and how the data is being collected for a given patient (e.g., in a datastore 511 implemented as a columnar SQL databases, NoSQL datastores, flat files, JSON documents and/or other possible data stores, as appropriate for given raw data type). The DCE 504 can also send a message to the SCE 502 letting it know that data has been updated for a patient and what new data items have been added so that the SCE 502 can pick up that data and use it to update the patient's PSO 501. In this manner, any BM measurement, any profile data edit, any SST answer, and any D-plan changes by a physician (e.g., adding rescue medications which may be needed for the D-plan's associated condition) can update the PSO 501 (including potentially updating derived values such as a patient's health score and compliance score), allowing the PSO 501 to function as a single version of all truth about a patient. The PSO 501 can be seen as a virtual representation of the actual patient (i.e., a representation of the patient person). In addition to being responsible for updating a PDO 509 as changes are made to a PIO 505 or available external sources 510 (including addition of new data sources), a DCE 504 could also be responsible for creating a new (generally empty) PDO 509 upon enrollment of a new patient (which PDO 509 would then preferably be populated as additional data such as the patient's smart devices and payer information is added during or after the sign up process). This can be achieved by implementing a DCE 504 as a set of rules which are updated when new data sources are added to the system. Preferably there will only be one such set of rules/DCE 504 per system implemented according to the architecture of FIG. 5, and that single set of rules/DCE 504 will be used to update, create and maintain the PDOs 509 for all enrolled patients.

In general, a DCE 504 will be configured to write/update data in a PDO 509 in the following circumstances:
1) when a new patient is added to the system
2) when a D-plan is associated with a patient, in which case the IDE 506 hands control to the DCE 504, and the DCE 504 has access to the PIO 505. The DCE 504 reads the PIO 505 to understand what all data capture modules (DCMs) have been assigned to the patient by the physician. This tells the DCE 504 what all data is being collected for the patient from the D-plans. The DCE 504 uses the PIO 505 information to write into the PDO 509 the list of all data items being collected for the patient, which could initially result in this list simply being the list of BM, SST and Edu modules active for the patient.
3) When a new D-plan is added or any changes are made to existing D-plans, the DCE 504 gets the message from the IDE 506. The DCE 504 then reads the updated PIO 505 and checks if any changes are required to the PDO 509 and makes them if required.
4) If new external data sources are added for a patient, such as Payer Data (e.g., information about the insurance provider a patient uses), EMR data, Pharmacy Data—the DCE 504 is instructed that a new data source has been added for the patient. Part of this instruction will preferably include:
  a. PatientID
  b. Data Source Name
  c. Data description elements described above
The DCE 504 then uses this information to update the patient PDO 509 by writing into the PDO 509 details about the new data source.

Preferably, in a system following the architecture of FIG. 5, when other components send a message to a DCE 504, the message will:
1) Identify patientID to access patient's PDO 509
2) Tell DCE one of following:
  a. New datasource being added
  b. New raw data for patient
3) If new a datasource is being added, provide:
  a. Data source name
  b. Internal or external
  c. Data format
  d. Data storage location
  e. Data privacy type: PHI or non-PHI
  f. Data access permissions: which modules can access the data (usually only SCE 502)
  g. Date source added
  h. Source expiration: usually none
4) If new raw data coming, provide the raw data type (e.g, BM, SST, Edu, external (payer, EMR, etc)). The DCE 504 will check the PDO 509 for where this data type needs to be stored, store the data in the required location and, once confirmation on data storage has been received from the relevant data store, hand over control to the SCE 502.

In addition to the items and data structures illustrated in FIG. 5, a system implemented using that architecture could also include certain shared data structures, such as lists of questions and instructions which could be read and write accessible by both an SCE 502 and ACE 503. Such lists could also be linked to individual patients, with each patient having different state flags indicating the state of the questions/instructions for him or her. Where it is present, a list of questions could be implemented as an array, e.g., an array identified as AllQuestions[ ]. Where such an array is present, it may be accessed indirectly, so AllQuestions[cough] would a question, even though 'cough' may not be the direct index value of the array. The array would preferably be susceptible to re-ordering without impacting the interface, and be associated with two Boolean flags for individual patients which could be accessed indirectly (e.g., via references to AllQuestions[q].Ask and AllQuestions[q].Asked (for any question q)). There may also be a function to initialize all Boolean fields for the questions to 'false.' Instructions could potentially be represented similarly (i.e., in an indirectly accessed array). Additionally, it is possible that instructions and/or questions could be organized into multiple arrays, which each might have their own flags. For example, instructions could be organized into AllTriageInstructions[ ] and MedicationInstructions[ ] arrays, where each element in the AllTriageInstructions[ ] array has a single flag (e.g., AllTriageInstructions[x].On), while medication instructions would not only have that flag but could also be organized as a two dimensional array with medications grouped by both type and specific medicine (e.g., MedicationInstructions[antibiotic].On=true could be executed as a general instruction, or MedicationInstructions[antibiotic][amoxicillin].On=true could be implemented as a specific instruction). In such a case, an SCE 502 could turn on MedicationInstructions[ ] as a result of questions being asked, and the ACE 503 would turn on TriageInstructions[ ] by looking at a SSTscore field in a PSO 501 and read the "On" instructions to determine what to tell the patient.

Figure 14:
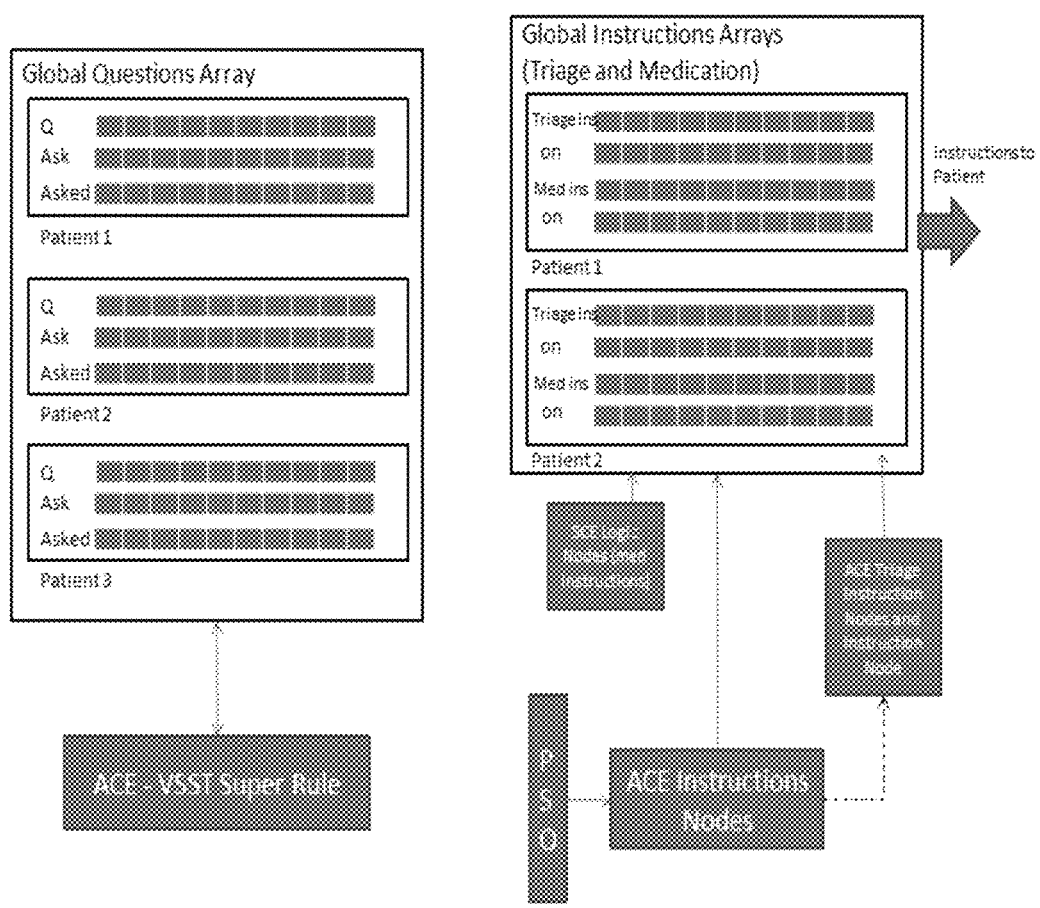
Figure 15:
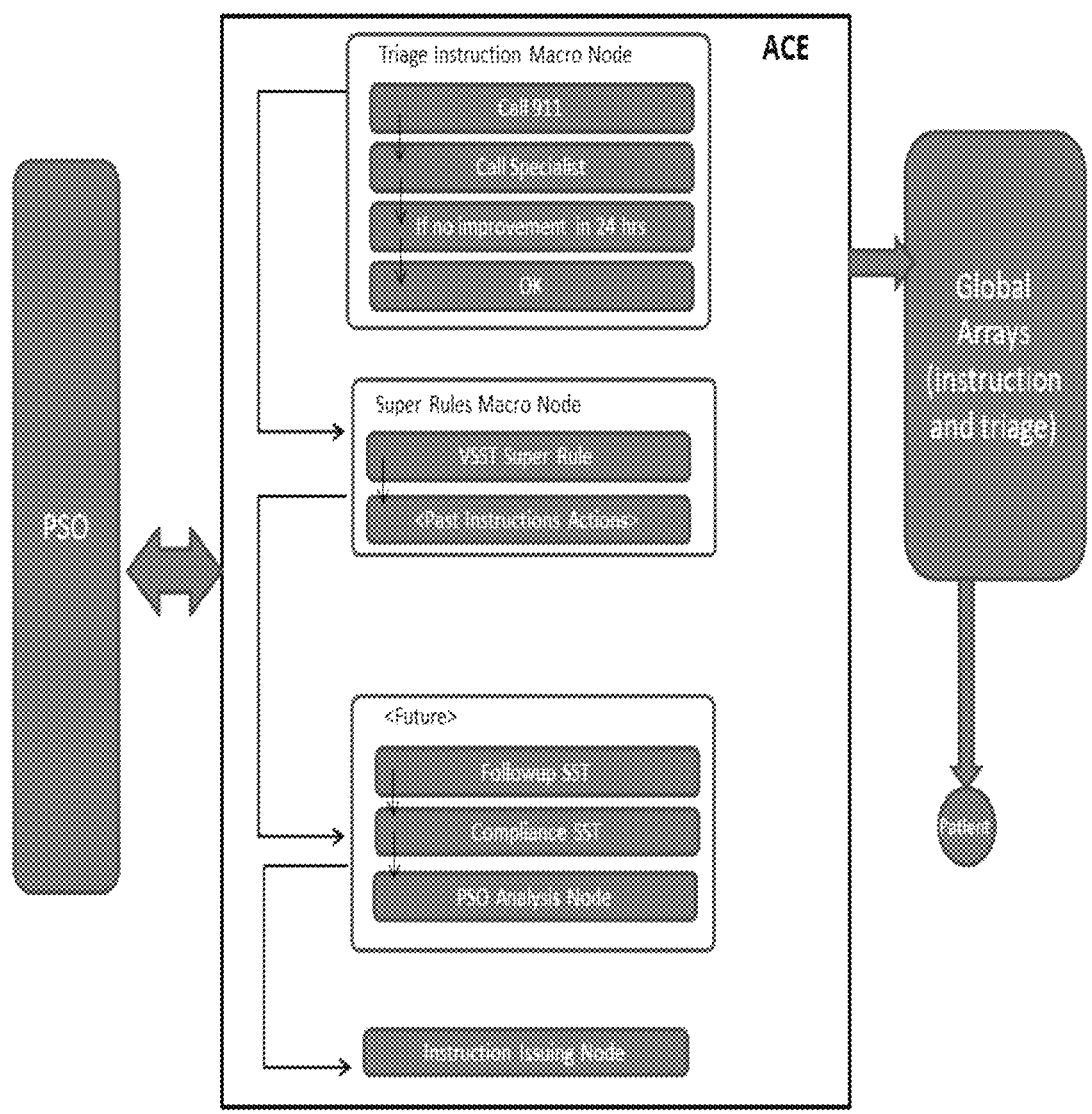
FIG. 15 illustrates a sequence of events as nodes are executed by an action controller engine.

An illustration of these types of global instruction data structures and their interactions with the components of FIG. 5 in an implementation using the virtual SST (VSST) concept is provided in FIG. 14. In this context, an ACE 503 can operate by running the triage nodes first, looking at the PSO.SSTscore field and activating the appropriate instruction (or instructions, if multiple instructions are on at once). Next a VSST session node runs. If the VSST flag is off, then the node does nothing. If VSST is on (i.e., a VSST session is being run), and if there are questions left to be asked (in the AllQuestions[ ] array), then this node sends the next question to the ICE 507, to be asked. If there are no questions left to be asked, then this node does nothing (in some embodiments, there may be logic to short-circuit evaluation, by stopping a VSST session 'early.'). The AllQuestions[ ] array keeps track of which questions will be asked, and which questions were already asked (in this VSST session). Next a PSO node runs. In some embodiments, this node may be empty. Finally an instruction node runs. This node checks if a VSST is running. If not (the flag is off) and there are instructions in the global instructions list(s), this node combines those instructions into one string message and sends to the ICE 507 for immediate release to the patient. This node resolves conflicts also, though the nature of this conflict resolution may vary from case to case, and in some embodiment may only be that the highest priority triage instruction is the only one sent. An illustration of this sequence of events as various nodes are executed by the ACE 503 is provided in FIG. 15.

To further illustrate potential applications of the disclosed technology, consider how the technology disclosed in this application could be used to support various front end interfaces for providing a unitary view of a patient's health to both the patient and his or her physician(s). As shown in FIG. 5, such interfaces could be provided to a patient or physician through an application running on a mobile device controlled by the relevant patient or physician. However, as will be immediately apparent to those of ordinary skill in the art in light of this disclosure, an architecture such as shown in FIG. 5 could easily be adapted to interact via website based interfaces, either as an alternative to, or in addition to interfaces provided by a mobile application. Similarly, it should be understood that patient centric data structures could be used in systems implemented to use the disclosed technology with components and/or architectures which do not follow the architecture of FIG. 5 (e.g., a virtual representation of a patient could be included in a system in which logic for determining how to update a patient's representation is included in SSTs, either in addition to, or as an alternative to, including it in rules for a state controller engine 502). Variations in data collected and stored are also possible. For example, in some embodiments collected outcomes data may be associated with so identifier for the data's source (e.g., if a physician enters a particular outcome for a patient, that outcome may be associated with a physicianID for that physician). This could be used to facilitate the storage (and potentially presentation) of data provided by patients separately from data provided by physicians, and could also be used for other purposes, such as generating or maintaining an audit log of changes.

Accordingly, in light of the potential for variations and modifications to the material described explicitly herein, the disclosure of this document should not be treated as implying limits on the protection provided by this document or any related document. Instead, the protection provided by a document which claims the benefit of or is otherwise related to this document should be understood as being defined by its claims, when the terms in those claims which are explicitly defined under the "Explicit Definitions" heading are given their explicit definitions, and when all other terms are given their broadest reasonable interpretation as shown by a general purpose dictionary. To the extent that the interpretation which would be given to the claims based on the above disclosure is in any way narrower than the interpretation which would be given based on the explicit definitions under the "Explicit Definitions" heading and the broadest reasonable interpretation as provided by a general purpose dictionary, the interpretation provided by the explicit definitions under the "Explicit Definitions" heading and broadest reasonable interpretation as provided by a general purpose dictionary shall control, and the inconsistent usage of terms in the specification shall have no effect, unless and to the extent that any particular claim or claims is amended to incorporate a narrower interpretation or limitation or a narrower interpretation or limitation is clearly and unambiguously adopted by Applicants during the course of prosecution of a particular claim or claims. It should also be understood that where the above disclosure refers to a species of a term that is defined generically in the Explicit Definitions or is otherwise encompassed by a definition in the Explicit Definitions, such reference in the above disclosure would support use of the full scope of the corresponding definition in the Explicit Definitions, including the species thereof. Thus, the use of a specific term in a particular context in the above disclosure would support use of the corresponding generic term as defined in the Explicit Definitions (as well as species thereof). By way of example, references to a "smartphone" in various contexts in the above disclosure would support use of the term "mobile computing device" and species thereof in such contexts.

Explicit Definitions

When used in the claims, "activity tracking device" refers to a type of "monitoring device" (defined infra) for monitoring and tracking fitness-related physiological parameters such as movement (e.g., distance walked or run, steps climbed), calories used, heart rate, sleep-related physiological parameters such as sleep duration, sleep depth, and any of a variety of others. An activity tracking device may use a three-dimensional accelerometer to sense user movement and measure steps taken, which it may use, sometimes together with user data, to calculate metrics such as distance walked, calories burned, floors climbed, and activity duration and intensity. Often an activity tracking device is a wearable electronic device that is or can be synchronized, in many cases wirelessly, to a computer or mobile device such as a smartphone. An activity tracking device may in some embodiments monitor activity in a room or within a home by means of heat-sensing (e.g., infrared), light-sensing, or other devices that detect movement or heat without necessarily being worn by or connected to the patient. Such devices may, for example, determine whether a patient has deviated from his or her normal level of activity within a home, failed to get out of bed, etc.

When used in the claims, "based on" should be understood to mean that something is determined at least in part by the thing that it is indicated as being "based on." When a claim is written to require something to be completely determined by a thing, it will be described as being "based EXCLUSIVELY on" the thing. Where the above disclosure refers to something being based on a thing or things, it should be understood that that "something" may, in certain embodiments, be based exclusively on that thing or things, or on any particular proper subset of such things.

When used in the claims, "behavioral data" should be understood to refer to any data pertaining to the way an individual acts, particularly those ways that may affect or reflect the individual's health, examples of "behavioral data" include, but are not limited to, data pertaining to: the individual's diet, physical activity, sleep, smoking, use of drugs with addictive potential, the way an individual interacts with a system implemented with the disclosed technology and components thereof (e.g., time spent accessing or otherwise engaging with educational materials), and/or compliance with a treatment plan.

When used in the claims a "body monitor" should be understood to refer to a general health measure which may not be specifically linked to a given disease. An example of a body monitor is a patient's temperature. A "dangerous" body monitor or outcome value is referred to as a "sign," which is simply a marker for an adverse value measurement and will typically be recorded as an event.

When used in the claims, a "computer" should be understood to refer to a device or group of devices (e.g., a device comprising a processor and a memory) capable of storing and executing instructions for performing one or more logical and/or physical operations on data to produce a result. A "computer" may include, for example, a single-core or multi-core microcontroller or microcomputer, a desktop, laptop or tablet computer, a smartphone, a server, or groups of the foregoing devices (e.g., a cluster of servers which are used in combination to perform operations on data for purposes such as redundancy and availability).

When used in the claims, "computer readable medium" should be understood to refer to any object, substance, or combination of objects or substances, capable of storing data or instructions in a form in which they can be retrieved and/or processed by a device. A computer readable medium should not be considered limited to any particular type or organization, and should be understood to include distributed and decentralized systems however they are physically or logically disposed, as well as storage objects of systems which are located in a defined and/or circumscribed physical and/or logical space.

When used in the claims, "condition" should be understood to refer to a circumstance of set of circumstances which can be used to characterize the state of an individual's health. Thus, a "condition" would include a health problem or abnormality or any state of abnormal or normal health or function for which an individual seeks or obtains care from a health care provider (e.g., any disease, disorder, or other diagnostic entity known to medical practitioners of ordinary skill). A "condition" would also include the state of good health which an individual might wish to maintain, but for which he or she would not necessarily seek or obtain care from a health care provider.

When used in the claims, in the context of health data "condition-centric" should be understood to mean that the relationship of the health data to a condition is the guiding principle used to determine which health data to obtain, analyze, store, and/or present to a user, and/or to determine how the health data are presented to a user.

When used in the claims, "data element" should be understood to refer to an individual unit of data, which may be indivisible or may consist of one or more data items. A data element may, for example, be something as simple as an individual measurement of a physiological variable such as body weight, a level of an analyte in a body fluid, or a patient's response to a yes/no question about the presence or severity of a symptom, or may be more complex, such as a medical image (e.g., an X-ray image), a pathology report, or the like.

When used in the claims, a "data element type" should be understood as being synonymous with a "type of data element," and should be understood to refer to a particular kind or category of data element. A data element type may have a specific name, e.g., "body weight", "cough severity change", "6 minute walk distance", or "chest X-ray" and a definition.

When used in the claims, to "determine" something should be understood to mean to produce or generate, compute, establish, or specify that thing. For example, something may be "determined" by selecting it from a group of alternatives or options, by analyzing data (e.g., by applying an algorithm to the data) to generate a result.

When used in the claims, "environmental data" refers to data concerning a patient's indoor or outdoor environment. In this context, "indoor environment" refers to inside the patient's home and/or workplace or such other place as the patient spends a significant amount of time (e.g., at least 10 hours per week), while "outdoor environment" refers to the environment outside of buildings, and can be measured with data such as outdoor temperature, and levels of pollen or pollutants or others substances in the air.

When used in the claims, "genotypic data" should be understood to refer to any data pertaining to the genetic makeup of a cell, population of cells, or an individual, usually (though not necessarily) with reference to a specific characteristic under consideration, specific gene or genes of interest, or specific nucleotide position(s) in a gene or genes of interest.

When used in the claims, "geographic data" should be understood to refer to data about a geographic region, which may include data about environmental conditions in a region or people in the region. It should be understood that "geographic data" may overlap with "population-based data" (defined infra) and that both "geographic data" and "population-based data" may include epidemiologic data, such as data about the prevalence of particular infectious diseases in the geographic region where a patient lives.

When used in the claims, "health care institution" should be understood as being synonymous with "health care facility" and should be understood to refer to an institution that provides health care to multiple persons on a systematic basis, such as a hospital, health clinic, health center, surgery center, skilled nursing facility, or physicians' practice.

When used in the claims, "health data" should be understood to refer to any data or information about or relating to an individual or group of individuals that is descriptive of, informative about, affects, or potentially affects the health of the individual or group of individuals in more than merely a tangential or insignificant way. Health data can include, for example, physiological data, symptom data, results of medical tests (e.g., clinical chemistry or other types of laboratory tests, imaging, pathology tests, or any other type of test that might be performed on a patient by or at the direction of a health care provider), genotypic data, behavioral data, environmental data, demographic data, demographic data, geographic data, population-based data.

When used in the claims, a "mobile computing device" (sometimes referred to simply as a "mobile device" herein) should be understood to refer to a computer adapted to be moved by a user and to be operable during such movement, such as by including a local power supply (e.g., a battery). Examples of "mobile computing devices" include, but are not limited to portable digital assistants (PDAs), "smartphones" (defined infra) tablet computers, and laptop computers. Often, a "mobile computing device" will weigh under about 1-2 pounds, e.g., between about 2-3 ounces and about 1.5 pounds. For example, a "smartphone" or PDA may weigh between about 3 ounces and about 6 ounces and have height and width dimensions in the range of less than about 7×5 inches and depth less than about 0.5-1.0 inch, though smaller or larger weight and/or dimensioned devices may also fall within the scope of "mobile computing device."

When used in the claims, "monitoring device" should be understood to refer to a device that can be used for detecting or measuring one or more physiological variables, environmental variables, or behavioral variables relevant to a patient. It should be understood that a "personal monitoring device" (defined infra) is included within the definition of "monitoring device" unless otherwise indicated. Examples of "monitoring devices" include body weight scales, pulse oximeters, blood pressure monitors, thermometers, activity tracking devices, heart rate monitors, blood glucose measuring devices (glucometers), stethoscopes, medication dispensers that in some way monitor medication usage, and any other devices capable of obtaining physiological data, environmental data, or behavioral data relating to a patient. Monitoring devices may be referred to as "body monitors", it being understood that such devices may collect data that pertains to a patient's environment or behaviors and are not limited to devices that collect data from or about a patient's body per se.

When used in the claims, an "outcome" should be understood to refer to health measurements or actions which may be, but are not necessarily, the ultimate results of a particular course of treatment or intervention or may serve as indicators of whether, or to what extent, a course of treatment or intervention is controlling or ameliorating a condition or symptom). Examples of outcomes include oxygen saturation for COPD, and hemoglobin A1C for diabetes mellitus. An outcome may be a result of a procedure or laboratory test or the fact that a procedure was performed on the patient (e.g., administration of a medication). In general, a given condition can have one or more outcomes associated with it. Some conditions may be associated with a single outcome, whereas other conditions may be associated with multiple outcomes. In general, a given outcome can be associated with one or more conditions. Some outcomes may be associated with a single condition, whereas other outcomes may be associated with multiple conditions.

When used in the claims, a "patient" should be understood to be an individual who seeks or receives health care from a health care provider.

When used in the claims, "personal monitoring device" should be understood to refer to a monitoring device that can be used by a patient in his or her daily life (i.e., while he or she is not under care in a health care facility).

When used in the claims, "physiological data" should be understood to refer to any qualitative or quantitative measurement of any indicator of a biological state, function, structure, process, response, or condition in a patient.

When used in the claims, "population-based data" should be understood to refer to data about groups of individuals, e.g., groups of patients having a particular condition or living in a particular geographic region. In this context, a geographic region may be a city, county, zip code area, state, or any other region as defined or used in an implementation of the disclosed technology. It should be understood that "population-based data" may overlap with "geographic data," and that both "population-based data" and "geographic data" may include epidemiologic data, such as data about the prevalence of particular conditions, e.g., infectious diseases, in the geographic region where a patient lives.

When used in the claims, a "set" should be understood to refer to a collection of zero or more things, which may be referred to as "elements" of the set. A "subset" of a set A is a set which does not include any elements that are not also in A. A subset of a set may include all the elements of the set.

When used in the claims, a "smartphone" should be understood as any mobile electronic device that combines the functions of a wireless phone and a computer within a single handheld unit and is capable of web browsing and running software applications. A "smartphone" can be understood in contrast with a "basic mobile phone" (i.e., a mobile phone that allows a user to make and receive calls but lacks the capability of executing software applications), or a "fixed phone" (i.e., a hard-wired or cordless phone that makes use of a fixed phone line).

When used in the claims, a "set" should be understood to refer to a collection of zero or more things, which may be referred to as "elements" of the set. A "subset" of a set A is a set which does not include any elements that are not also in A. A subset of a set may include all the elements of the set.

When used in the claims, a "symptom" should be understood to include things like headache, impaired ability to walk, shortness of breath and other items related to subjective aspects of patient health about which data can be collected.

When used in the claims, "means for responding to a patient event" should be understood as a means+function limitation as provided for in 35 U.S.C. § 112(f), in which the function is "responding to a patient event" and the corresponding structure is an interface controller engine ("ICE") as described herein.

When used in the claims, "means for creating, updating, and maintaining a patient interface data set" should be understood as a means+function limitation as provided for in 35 U.S.C. § 112(f), in which the function is "creating, updating, and maintaining a patient interface data set" and the corresponding structure is an interface design engine ("IDE") as described herein.

When used in the claims, "means for controlling data" should be understood as a means+function limitation as provided for in 35 U.S.C. § 112(f), in which the function is "controlling data" and the corresponding structure is a data controller engine ("DCE") as described herein.

When used in the claims, "means for maintaining a patient state data set" should be understood as a means+function limitation as provided for in 35 U.S.C. § 112(f), in which the function is "maintaining a patient state data set" and the corresponding structure is a state controller engine ("SCE") as described herein.

When used in the claims, "means for consolidating a set of relevant rules" should be understood as a means+function limitation as provided for in 35 U.S.C. § 112(f), in which the function is "consolidating a set of relevant rules" and the corresponding structure is a action controller engine ("ACE") as described herein.

When used in the claims, "means for delivering messages to patients" should be understood as a means+function limitation as provided for in 35 U.S.C. § 112(f), in which the function is "delivering messages to patients" and the corresponding structure is an engagement engine ("EE") as described herein.

What is claimed is:

1. A system for assembling, analyzing, facilitating access to, and performing actions based on health information, the system comprising non-transitory computer readable medium storing a plurality of patient state objects, wherein each patient state object:
   a) corresponds to a different patient from a plurality of patients registered with the system;
   b) provides a holistic and continuously updateable view of the patient to whom it corresponds; and
   c) is a data structure adapted to store, for the patient to whom it corresponds, data comprising:
      i) physiological data regarding that patient, wherein the physiological data each patient state object is adapted to store for its corresponding patient comprises:
         A) an overall health score for the corresponding patient;
         B) a heath score trend for the corresponding patient;
         C) a health score volatility for the corresponding patient;
         D) a general hospitalization risk for the corresponding patient;
         E) for each of a plurality of conditions:
            I) a risk level for the corresponding patient for that condition; and
            II) a condition exacerbation risk for the corresponding patient for that condition;
         F) for each of a plurality of body monitors:
            I) an urgency score for the corresponding patient for that body monitor; and
            II) a risk level for the corresponding patient for that body monitor; and
         G) an overall exacerbation risk for the corresponding patient;
      ii) behavioral data regarding that patient, wherein the behavioral data each patient state object is adapted to store for its corresponding patient comprises:
         A) compliance by the corresponding patient with requests for survey data;
         B) compliance by the corresponding patient with using medications as directed;
         C) a compliance level score for the corresponding patient;
         D) a recent compliance level score for the corresponding patient;
         E) a compliance score trend for the corresponding patient;
         F) a compliance score volatility for the corresponding patient; and
         G) for each of a plurality of body monitors, a compliance score for providing measurements from that body monitor; and
      iii) demographic data regarding that patient;
   d) stores all health data used by the system for performing actions for the patient to which it corresponds.

2. The system of claim 1, wherein each patient state object is a multidimensional vector accessible using an identifier for the corresponding patient as an argument to patient state object retrieval function.

3. The system of claim 1, wherein:
   a) the demographic data each patient state object is adapted to store for its corresponding patient comprises:
      i) age of the corresponding patient;
      ii) gender of the corresponding patient;
      iii) income level of the corresponding patient;
      iv) education level of the corresponding patient;
      v) environment of the corresponding patient; and
      vi) location of the corresponding patient;
   b) the physiological data each patient state object is adapted to store for its corresponding patient comprises:
      i) allergies of the corresponding patient; and
      ii) medications taken by the corresponding patient.

4. The system of claim 1, wherein:
   a) the system comprises a state controller engine ("SCE") having a plurality of rules for updating patient state objects;
   b) for each patient state object from the plurality of patient state objects, the system is adapted to cause the SCE to evaluate rules for updating patient state objects based on one or more of:
      i) receipt of new data regarding the patient corresponding to that patient state object; and
      ii) a periodically scheduled trigger for determining updates to that patient state object based on historical data regarding that patient state object.

5. The system of claim 4, wherein the system has only a single SCE, and all updates to all patient state objects from the plurality of patient state objects are performed using that SCE.

6. The system of claim 4 wherein the system is configured to use the SCE to continuously update the plurality of patient state objects as new data becomes available.

7. The system of claim 1, wherein:
   a) the system comprises an action controller engine (ACE) having a plurality of rules for determining actions to perform based on data from patient state objects;
   b) for each patient state object from the plurality of patient state objects, the system is adapted to cause the ACE to evaluate rules for taking action based on data from patient state objects based on one or more of:

i) receipt of a message indicating an update to that patient state object; and
ii) a time based trigger for running rules in a batch process.

8. The system of claim 7, wherein the ACE has rules adapted to, based on evaluation of rules with data from a patient state object corresponding to a specific patient, cause the system to perform actions comprising:
a) communicating with the specific patient by sending a message to a computer of the specific patient;
b) communicating with a healthcare provider of the specific patient by sending a message to a computer of the healthcare provider of the specific patient;
c) communicating with a caregiver of the specific patient by sending a message to a computer of the caregiver of the specific patient;
d) requesting health data from the specific patient;
e) requesting an update to a body monitor measurement for the specific patient;
f) recommending the specific patient seek medical attention by performing an action selected from a group consisting of:
   i) calling 911; and
   ii) calling a physician;
g) recommending that the specific patient take a medication;
h) sending a reminder message to the specific patient; and
i) adjusting a timing or frequency for collecting data from the specific patient.

9. The system of claim 7 or claim 8 wherein:
a) the plurality of rules for the ACE are organized into a plurality of nodes;
b) the plurality of nodes into which the rules for the ACE are organized comprise a plurality of macro nodes, wherein each macro node:
   i) is dedicated to a specific rule type; and
   ii) comprises a set of micro nodes, wherein each micro node:
      A) comprises one or more rules which, when that micro node is run for a patient, are evaluated with data from the patent state object corresponding to the patient for which that micro node is run;
      B) has a single output instruction it could potentially issue upon being run; and
      C) has a local priority establishing an order in which it is run in the macro node it is comprised by.

10. The system of claim 9, wherein:
a) the ACE is configured to perform a smart symptom tracker ("SST") session for a patient by performing a set of acts comprising:
   i) running each macro node from the plurality of macro nodes in a predetermined sequence, wherein, for each macro node, running that macro node comprises running the micro nodes comprised by that macro node for the patient for which the SST session is being performed in descending order of the local priorities of those micro nodes;
   ii) adding all output instructions issued by the micro nodes comprised by the macro nodes while running the macro nodes in the SST session for the patient to a stack; and
   iii) holding the output instructions issued by the micro nodes comprised by the macro nodes while running the macro nodes in the SST session for the patient in the stack until the SST session for the patient is concluded;
b) the system is adapted to, after the SST session for the patient is concluded, provide the patient for whom the SST session was performed with information specified by the output instructions added to the stack during the SST session for the patient via an interface on a computing device associated with the patient for whom the SST session was performed.

11. The system of claim 10 wherein the SST session is a virtual SST session wherein:
a) the ACE is adapted to evaluate, at initiation of the virtual SST session, a rule for modifying the patient state object corresponding to the patient for whom the virtual SST session is performed to indicate that the virtual SST session is in progress for that patient;
b) the system is configured to, during performance of the virtual SST session for the patient, implement any modifications to the patient state object corresponding to the patient for which the virtual SST sessions is performed triggered by evaluation of rules during the virtual SST session; and
c) the ACE is adapted to conclude the virtual SST session for the patient by evaluating a rule for modifying the patient state object corresponding to the patient for whom the virtual SST session is performed to indicate that no virtual SST session is in progress for that patient.

12. The system of claim 11 wherein;
a) the system comprises an output instructions data structure comprising all output instructions which could potentially be issued by the micro nodes comprised by the macro nodes while running the macro nodes in the SST session for the patient;
b) adding all output instructions issued by the micro nodes comprised by the macro nodes while running the macro nodes in the SST session for the patient to the stack comprises, for each issued output instruction, modifying information in the output instructions data structure for that output instruction to indicate that that instruction should be issued to the patient for whom the virtual SST session is performed;
c) providing the patient for whom the virtual SST session was performed with information specified by the output instructions added to the stack during the SST session for the patient comprises:
   i) analyzing the output instructions which information in the output instructions data structure indicates should be issued to the patient for whom the virtual SST session was performed for conflicts;
   ii) modifying information in the output instructions data structure for any conflicting output instructions to indicate that the conflicting instructions should not be issued to the patient for whom the virtual SST session was performed; and
   iii) providing the patient for whom the virtual SST session was performed with information specified by the output instructions which information in the output instructions data structure indicates should be issued to the patient for whom the virtual SST session was performed.

13. The system of claim 12 wherein the output instructions data structure is an array.

14. The system of claim 10, wherein the plurality of macro nodes comprises:
a) a macro node dedicated to triage instruction rules, wherein the macro node dedicated to triage instruction rules is first in the predetermined sequence and comprises:

i) a micro node comprising one or more rules which, when evaluated, could potentially issue an instruction to call 911, wherein the local priority of this micro node is greater than the local priority of all other micro nodes within the macro node dedicated to triage instructions;

ii) a micro node comprising one or more rules which, when evaluated, could potentially issue an instruction to call a physician, wherein the local priority of this micro node is greater than the local priority of all other micro nodes within the macro node dedicated to triage instructions, with the exception of the micro node comprising one or more rules which, when evaluated, could potentially issue an instruction to call 911;

iii) a micro node comprising one or more rules which, when evaluated, could potentially issue an instruction to take action if there is no improvement after 24 hours, wherein the local priority of this micro node is less than the priority of the micro node comprising one or more rules which, when evaluated, could potentially issue an instruction to call a physician but greater than the local priority of all other micro nodes within the macro node dedicated to triage instructions; and iv) a micro node comprising one or more rules which, when evaluated, could potentially issue an instruction that no triage action should be taken, wherein the local priority of this micro node is less than the priority of all other micro nodes within the macro node dedicated to triage instructions;

b) a macro node dedicated to medication instruction rules, wherein the macro node dedicated to medication instruction rules is second in the predetermined sequence and comprises:

i) a micro node comprising one or more rules which, when evaluated, could potentially issue an instruction to use a medical device, wherein the local priority of this micro node is greater than the local priority of all other micro nodes within the macro node dedicated to medication instructions; and ii) a micro node comprising one or more rules which, when evaluated, could potentially issue an instruction to take a medication, wherein the local priority of this micro node is greater than the local priority of all other micro nodes within the macro node dedicated to medication instructions, with the exception of the micro node comprising one or more rules which, when evaluated, could potentially issue an instruction to use a medical device;

and c) a macro node dedicated to future instruction rules, wherein at least one micro node comprised by the macro node dedicated to future instruction rules comprises one or more rules which, when evaluated, could potentially trigger a future SST session after conclusion of the SST session being performed for the patient.

15. The system of claim 14, wherein:
a) the medical device is a nebulizer; and
b) the medication is a steroid.

16. The system of claim 9, wherein the system is adapted to, during the SST session for the patient, provide one or more prompts requesting information to the patient for whom the SST session is performed.

17. The system of claim 7, wherein:
a) the plurality of rules for the ACE are organized into a plurality of nodes;
b) each node from the plurality of nodes:
  i) comprises one or more of the rules from the ACE;
  ii) has sequencing data indicating, when data is to be evaluated by rules from multiple nodes, an order of activation for the nodes comprising the rules by which the data is to be evaluated;
c) the system is adapted to maintain node type data indicating, for each node from the plurality of nodes, types of data to be evaluated by rules from that node.

18. The system of claim 17, wherein:
a) when a data item in a patent state object is updated, the system is configured to evaluate that data item with only the nodes indicated by the node type data as comprising rules for evaluating the data type of the data item updated in the patient state object; and
b) the node type data indicates a node as comprising rules for evaluating a particular data type by indicating either:
  i) the node comprises rules which are specific to the particular data type; or
  ii) the node comprises rules which are general rules applying to multiple data types.

19. The system of claim 17, wherein the node type data is an index comprised by the ACE.

20. The system of claim 7, wherein the system is configured to use the ACE to flexibly react to patient data in a real time manner.

* * * * *